United States Patent
Ishii et al.

(12)

(10) Patent No.: US 6,229,023 B1
(45) Date of Patent: May 8, 2001

(54) PROCESS FOR COOXIDIZING ORGANIC COMPOUNDS, PROCESS FOR PRODUCING EPOXY COMPOUNDS AND PROCESS FOR PRODUCING ESTERS OR LACTONES

(75) Inventors: Yasutaka Ishii, Takatsuki; Tatsuya Nakano, Himeji, both of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/424,315

(22) PCT Filed: Mar. 23, 1999

(86) PCT No.: PCT/JP99/01464

§ 371 Date: Nov. 22, 1999

§ 102(e) Date: Nov. 22, 1999

(87) PCT Pub. No.: WO99/50204

PCT Pub. Date: Jul. 10, 1999

(30) Foreign Application Priority Data

Mar. 27, 1998 (JP) .................................................. 10-100459
Apr. 16, 1998 (JP) .................................................. 10-124215
Jan. 28, 1999 (JP) .................................................. 10-020325

(51) Int. Cl.[7] ........................ C07D 313/00; C07D 309/00
(52) U.S. Cl. ......................... 549/266; 549/273; 549/295; 549/518; 560/129
(58) Field of Search ............................... 560/129; 549/518, 549/266, 273, 295

(56) References Cited

FOREIGN PATENT DOCUMENTS

| | | |
|---|---|---|
| 9-327626 | 12/1997 | (JP) . |
| 10-286467 | 10/1998 | (JP) . |
| 10-309469 | 11/1998 | (JP) . |
| 10-310543 | 11/1998 | (JP) . |

Primary Examiner—Amelia Owens

(57) ABSTRACT

According to the inventive co-oxidation process of organic compounds, (A) a compound selected from (A1) a compound having a non-aromatic ethylenic bond and (A2) a ketone or an alcohol corresponding to the ketone is oxidized by molecular oxygen in the presence of N-hydroxyphthalimide or another imide compound and in the coexistence of (B) a compound oxidizable by the imide compound and oxygen and different from the compound (A). As the compound (B), (a) primary or secondary alcohols (e.g., benzhydrol, cyclohexanol), (b) compounds each having a carbon-hydrogen bond at the adjacent position to an unsaturated bond (e.g., tetralin, ethylbenzene) and the like can be used. According to this process, a corresponding epoxy compound from the compound (A1) having a non-aromatic ethylenic bond, and a corresponding ester or lactone from the ketone or its corresponding alcohol (A2) can be obtained in satisfactory yields.

17 Claims, No Drawings

PROCESS FOR COOXIDIZING ORGANIC COMPOUNDS, PROCESS FOR PRODUCING EPOXY COMPOUNDS AND PROCESS FOR PRODUCING ESTERS OR LACTONES

This application is the national phase under 35 U.S.C. §371 of PCT International Application No. PCT/JP99/01464 which has an International filing date of Mar. 23, 1999, which designated the United States of America.

TECHNICAL FIELD

The present invention relates to a process for the co-oxidation of organic compounds, a process for the production of epoxy compounds, and a process for the production of esters or lactones. More particularly, it relates to a process of co-oxidizing an alkene, a cycloalkane or another compound having a non-aromatic ethylenic bond, or a ketone or an alcohol, by molecular oxygen in the coexistence of another organic compound to give a corresponding oxide, that is, an epoxy compound, or an ester or a lactone.

BACKGROUND ART

Chain or cyclic epoxy compounds, esters and lactones are important compounds as pharmaceuticals, perfumes, dyes, organic intermediates and materials for polymeric resins.

Epoxy compounds and esters or lactones are, even though they are different in reaction materials, common in that they are produced by oxidation reaction using perbenzoic acid, peracetic acid, trifluoroperacetic acid or another peracid. For example, an epoxy compound is produced by the reaction of an alkene, a cycloalkane or another compound having a non-aromatic ethylenic bond with the peracid. An ester or lactone is obtained by the reaction of a chain or cyclic ketone with the peracid, i.e., by a so-called Baeyer-Villiger rearrangement (oxidation). The peracid is, however, unstable and should be handled with extreme caution. In addition, an equivalent amount of a carboxylic acid is by-produced in the reaction using the peracid.

As a production process for epoxy compounds is known a process of allowing a hypohalogenous acid to act on an unsaturated compound to give a halohydrin, and treating the halohydrin with an alkali. This process is, however, unable to be applied to olefins each having a complicated structure. Furthermore, there is known a process of allowing a microorganism to act on an unsaturated compound in the presence of oxygen to give a corresponding epoxy compound. Such a process using a microorganism is, however, disadvantageous in productivity, because the concentration of a substrate cannot generally be increased.

Japanese Unexamined Patent Publication No. 9-327626 discloses a process of oxidizing an unsaturated chain hydrocarbon or an alkene, cyclohexanone or cyclohexanol by molecular oxygen in the presence of an imide compound. According to this literature, however, an unsaturated chain hydrocarbon or an alkene predominantly gives a ketone or an alcohol in which the adjacent position to a double bond is oxidized, and a corresponding epoxy compound is not obtained. Cyclohexanone or cyclohexanol predominantly gives a corresponding dicarboxylic acid, but no corresponding ester or lactone.

DISCLOSURE OF INVENTION

Accordingly, it is an object of the invention to provide a process which can oxidize alkenes, cycloalkenes and other compounds each having a non-aromatic ethylenic bond or chain or cyclic ketones, under mild conditions, by simple operations with efficiency.

Another object of the invention is to provide a process which can produce corresponding epoxy compounds from compounds each having a non-aromatic ethylenic bond, under mild conditions, by simple operations in high yield.

It is a further object of the invention to provide a process which can produce, under mild conditions, corresponding esters or lactones by the oxidation of ketones or their precursors, secondary alcohols, with facility and efficiency.

After intensive investigations to achieve the above objects, the present inventors found that an effective solution is the oxidation of a compound having a non-aromatic ethylenic bond or a ketone (or its alcohol) by molecular oxygen with the use of an imide compound having a specific structure as a catalyst and in the coexistence of a specific compound, or the oxidation of a secondary alcohol by molecular oxygen in the presence of an imide compound catalyst having a specific structure and subsequent treatment with an acid. By this configuration, an epoxidation reaction preferentially proceeds to give a corresponding epoxy compound in satisfactory yield when a compound having a non-aromatic ethylenic bond is used as a material, or a so-called Baeyer-Villiger type reaction proceeds to give a corresponding ester or lactone with efficiency when a ketone or a secondary alcohol is used as a material. The present invention has been accomplished based upon the above findings.

To be more specific, the invention provides a process for the co-oxidation of organic compounds, the process including the step of:

oxidizing (A) a compound selected from (A1) a compound having a non-aromatic ethylenic bond, and (A2) a ketone represented by the following formula (2):

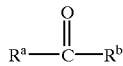

(2)

(wherein each of $R^a$ and $R^b$ is, identical to or different from each other, an organic group having a carbon atom at a bonding size with the adjacent carbonyl carbon atom, where $R^a$ and $R^b$ may be combined to form a ring with the adjacent carbonyl carbon atom)

or an alcohol corresponding to the ketone, by molecular oxygen in the presence of an imide compound represented by the following formula (1):

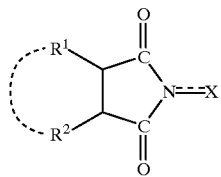

(1)

(wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond, or an aromatic or non-aromatic ring; X is an oxygen atom or a hydroxyl group; and one or two N-substituted cyclic imido groups indicated in the formula (1) may further be formed on the aforementioned $R^1$, $R^2$, or on the double bond or aromatic or non-aromatic ring formed together by $R^1$ and $R^2$) and in the coexistence of (B) a compound being oxidizable by the imide compound and oxygen and being different from the compound (A).

$R^1$ and $R^2$ in the imide compound represented by the formula (1) may be combined to form an aromatic or non-aromatic 5- to 12-membered ring, and $R^1$ and $R^2$ may be combined to form a cycloalkane ring which may have a substituent, a cycloalkene ring which may have a substituent, a bridged carbocyclic ring which may have a substituent, or an aromatic ring which may have a substituent.

The compound (A1) having a non-aromatic ethylenic bond includes, but is not limited to, (A11) chain hydrocarbons each having an ethylenic bond and having 2 to 30 carbon atoms, (A12) compounds each having a 3- to 30-membered cycloalkene ring, (A13) unsaturated bridged cyclic hydrocarbons, and (A14) heterocyclic compounds each having a non-aromatic ethylenic bond as a constitutive element of its ring.

The ketone represented by the formula (2) includes, but is not limited to, cyclohexanones and other 3- to 20-membered cycloalkanones.

As the compound (B), use may be made of at least one compound selected from (a) primary or secondary alcohols, (b) compounds each having a carbon-hydrogen bond at the adjacent position to an unsaturated bond, (c) compounds each having a methine carbon atom, (d) cycloalkanes, (e) non-aromatic heterocyclic compounds each having a carbon-hydrogen bond at the adjacent position to a hetero atom, (f) conjugated compounds, (g) aromatic hydrocarbons, (h) thiols, (i) ethers, (j) sulfides, (k) aldehydes or thioaldehydes, and (l) amines.

In the process for the co-oxidation of organic compounds, the oxidation may be performed further in the presence of (C) at least one compound selected from the group consisting of (C1) compounds each having a carbonyl group combined with an electron attractive group, (C2) metallic compounds, and (C3) organic salts each composed of a polyatomic cation or a polyatomic anion and its counter ion, the polyatomic cation or anion containing a Group 15 or Group 16 element of the Periodic Table of Elements, the element having at least one organic group bonded thereto.

The invention provides, in another aspect, a process for the production of epoxy compounds, the process including the step of: oxidizing (A1) a compound having a non-aromatic ethylenic bond by molecular oxygen in the presence of the imide compound represented by the formula (1) to form a corresponding epoxide, wherein the compound (A1) having a non-aromatic ethylenic bond is oxidized in the coexistence of (B1) a compound being oxidizable by the imide compound and oxygen and being different from the compound (A1).

In a further aspect, the invention provides a process for the production of esters or lactones [hereinafter may be referred to as "the production process 1 of esters or lactones"], the process including the step of: oxidizing (A2) a ketone represented by the following formula (2) or an alcohol corresponding to the ketone, byrmolecular oxygen in the presence of the imide compound represented by the formula (1), together with (B2) a compound being oxidizable by the imide compound and oxygen and being different from the compound (A2) to give a compound represented by the following formula (3):

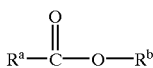

(wherein each of $R^a$ and $R^b$ is, identical to or different from each other, an organic group having a carbon atom at a bonding site with the adjacent carbonyl carbon atom or oxygen atom, where $R^a$ and $R^b$ may be combined to form a ring with the adjacent carbonyl carbon atom and oxygen atom).

In this process, a ketone represented by the formula (2) may be used as a substrate, and a secondary alcohol corresponding to the ketone may be used as the compound (B2)

The invention provides, in yet another aspect, a process for the production of esters or lactones [hereinafter may be referred to as "the production process 2 of esters or lactones"], the process including the steps of: oxidizing a secondary alcohol represented by the following formula (4):

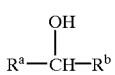

(wherein each of $R^a$ and $R^b$ is, identical to or different from each other, an organic group having a carbon atom at a bonding site with the adjacent carbon atom, where $R^a$ and $R^b$ may be combined to form a ring with the adjacent carbon atom) by molecular oxygen in the presence of the imide compound represented by the formula (1), and treating the oxidized compound with an acid to give a compound represented by the following formula (3):

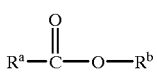

(wherein each of $R^a$ and $R^b$ is, identical to or different from each other, an organic group having a carbon atom at a bonding site with the adjacent carbonyl carbon atom or oxygen atom, where $R^a$ and $R^b$ may be combined to form a ring with the adjacent carbonyl carbon atom and oxygen atom).

In the process just mentioned above, the oxidation may be performed in the presence of a ketone. A ketone corresponding to the secondary alcohol represented by the formula (4) can be used as the ketone, and a Lewis acid may be used as the acid. in this production process, a 3- to 20-membered cycloalkanol (e.g., a cyclohexanol) may be oxidized by molecular oxygen in the presence of the imide compound represented by the formula (1), and the oxidized compound may be treated with an acid to give a corresponding lactone (e.g., an ε-caprolactone).

In the present description, the "compound having a non-aromatic ethylenic bond", "ketone, or its corresponding alcohol", or "secondary alcohol" each used as a reactant in the aforementioned individual processes may simply be referred to as a "substrate". The "compound (B) being oxidizable by the imide compound and oxygen and being different from the compound (A)" may be referred to as a "co-oxidizing agent".

BEST MODE FOR CARRYING OUT THE INVENTION

[Substrate]

The compounds (A1) each having a non-aromatic ethylenic bond to be used as the substrate include, for example, (A11) chain hydrocarbons each having an ethylenic bond, (A12) compounds each having a cycloalkene ring, (A13) unsaturated bridged cyclic hydrocarbons, and (A14) heterocyclic compounds each having a non-aromatic ethylenic bond as a constitutive element of its ring. Each of these compounds may have a plurality of non-aromatic ethylenic bonds in the molecule.

The chain hydrocarbons (A11) each having an ethylenic bond include, but are not limited to, ethene, propene, 1-butene, 2-butene, 1-pentene, 2-pentene, 2,4,4-trimethyl-2-pentene, 1-hexene, 2-hexene, 2,3-dimethyl-2-butene, 3-hexene, 1-heptene, 1-octene, 2-octene, 3-octene, 1-nonene, 2-nonene, 1-decene, 1-undecene, 1-dodecene, 1-hexadecene, 1-octadecene, and other alkenes; 1,4-butadiene, 1,5-hexadiene, 1,6-heptadiene, 1,7-octadiene, 2,6-octadiene, and other alkadienes; undecatriene, dodecatriene, and other alkatrienes. The chain hydrocarbons (A11) may each have, for example, about 2 to 30, preferably about 2 to 20, and more preferably about 2 to 12 carbon atoms.

These chain hydrocarbons (A11) may have a substituent such as a halogen atom, a hydroxyl group, a mercapto group, an oxo group, a substituted oxy group (e.g., an alkoxy group, an aryloxy group, an acyloxy group), a substituted thio group, a carboxyl group, a substituted oxycarbonyl group, a substituted or unsubstituted carbamoyl group, a cyano group, a nitro group, a substituted or unsubstituted amino group, a sulfo group, an alkynyl group, an alicyclic hydrocarbon group, an aromatic hydrocarbon group or a heterocyclic group.

Concrete examples of the chain hydrocarbons (A11) each having a substituent include, but are not limited to, 3-hexen-1-ol, 2-hexen-1-ol, 1-octen-3-ol, and other compounds each having a hydroxy group and an ethylenic bond; 1-acetoxy-3,7-dimethyl-2,6-octadiene, and other compounds each having an acyloxy group and an ethylenic bond. If the chain hydrocarbons (A11) each having an ethylenic bond have geometric isomers, any of E-isomers, Z-isomers and mixtures thereof may be used.

The compounds (A12) each having a cycloalkene ring include, but are not limited to, cyclopropene, cyclobutene, cyclopentene, cyclohexene, cycloheptene, cyclooctene, cyclononene, cyclodecene, cycloundecene, cyclododecene, and other cycloalkenes; 1,4-cyclohexadiene, 1,4-cycloheptadiene, cyclodecadiene, cyclododecadiene, and other cycloalkadienes: cyclodecatriene, and other cycloalkatrienes; cyclododecatetraene, and other cycloalkateteraenes. The cycloalkane ring may have, for example, about 3 to 30, preferably about 3 to 20, and more preferably about 3 to 12 (especially 5 to 10) members.

The cycloalkene ring may have a substituent including a halogen atom, a hydroxyl group, a mercapto group, an oxo group, a substituted oxy group (e.g., an alkoxy group, an aryloxy group, an acyloxy group), a substituted thio group, a carboxyl group, a substituted oxycarbonyl group, a substituted or unsubstituted carbamoyl group, a cyano group, a nitro group, a substituted or unsubstituted amino group, a sulfo group, an alkyl group (e.g., methyl, ethyl, t-butyl group or another $C_1-C_4$ alkyl group), an alkenyl group (e.g., a $C_2-C_4$ alkenyl group), an alkynyl group (e.g., a $C_2-C_4$ alkynyl group), an alicyclic hydrocarbon group, an aromatic hydrocarbon group, or a heterocyclic group. Separately, an aromatic or non-aromatic carbocyclic ring, or an aromatic or non-aromatic heterocyclic ring may be condensed to the cycloalkene ring. As practical examples of the compounds (A12) each having a substituent on its ring, there may be mentioned limonene, 1-p-menthene, 3-p-menthene, carveol, and other terpenes.

The unsaturated bridged cyclic hydrocarbons (A13) include, but are not limited to, bicyclo[2.2.1]-hept-2-ene, bicyclo[3.2.1]oct-2-ene, α-pinene, 2-bornene, and other terpenes.

As the heterocyclic compounds (A14) each having a non-aromatic ethylenic bond as a constitutive element of its ring, there may be mentioned 3,6-dihydro-2H-pyran, and 1,2,5,6-tetrahydropyridine, for example. These compounds may each have a similar substituent, or an aromatic or non-aromatic carbocyclic ring or an aromatic or non-aromatic heterocyclic ring may be condensed thereto, as in the cycloalkene ring.

In the ketones of the formula (2) as the substrate, the "organic group having a carbon atom at a bonding site with the adjacent carbonyl carbon atom" represented by $R^a$ and $R^b$ includes hydrocarbon groups and heterocyclic groups. As such hydrocarbon groups, there may be mentioned, for instance, methyl, ethyl, propyl, isopropyl, butyl, isobutyl, s-butyl, t-butyl, pentyl, neopentyl, hexyl, octyl, decyl, dodecyl, pentadecyl, vinyl, allyl, 1-hexenyl, ethynyl, and 1-butynyl groups, and other aliphatic hydrocarbon groups (alkyl groups, alkenyl groups or alkynyl groups) each having about 1 to 20 carbon atoms (preferably 1 to 15 carbon atoms, and more preferably 1 to 10 carbon atoms); cyclopropyl, cyclobutyl, cyclopentyl, cyclopentenyl, cyclohexyl, cyclohexenyl, cyclooctyl, and cyclododecyl groups, and other alicyclic hydrocarbon groups (cycloalkyl groups or cycloalkenyl groups) each having about 3 to 20 members (preferably 3 to 15 members, and more preferably 5 to 8 members); phenyl and naphthyl groups, and other aromatic hydrocarbon groups each having about 6 to 18 carbon atoms.

Heterocyclic rings corresponding to the heterocyclic groups include, but are not limited to, heterocyclic rings each containing an oxygen atom as a hetero atom (e.g., tetrahydrofuran, chroman, isochroman, furan, oxazole, isoxazole, 4-oxo-4H-pyran, benzofuran, isobenzofuran, and 4-oxo-4H-chromene), heterocyclic rings each containing a sulfur atom as a hetero atom (e.g., thiophene, thiazole, isothiazole, thiadiazole, 4-oxo-4H-thiopyran, and benzothiophene), heterocyclic rings each containing a nitrogen atom as a hetero atom (e.g., pyrrolidine, piperidine, piperazine, morpholine, indoline, pyrrole, pyrazole, imidazole, triazole, pyridine, pyridazine, pyrimidine, pyrazine, indole, quinoline, acridine, naphthyridine, quinazoline, purine).

The rings which may be formed by $R^a$ and $R^b$ combined together with the adjacent carbonyl carbon atom include cyclopropane, cyclobutane, cyclopentane, cyclopentene, cyclohexane, cyclohexene, cyclooctane, and cyclododecane rings, and other alicyclic hydrocarbon rings (cycloalkane rings or cycloalkene rings) each having about 3 to 20 members (preferably 3 to 15 members, and more preferably 3 to 12 members); norbornane ring, norbornene ring, adamantane ring, and other bridged cyclic hydrocarbon rings or bridged cyclic heterocyclic rings each having about 2 to 4 rings; tetrahydrofuran, chroman, isochroman, pyrrolidine, piperidine, and other non-aromatic heterocyclic rings each having about 5 to 8 members.

The organic groups and the rings which may be formed by $R^a$ and $R^b$ combined with the adjacent carbon atom may have a substituent. Such substituents include, but are not limited to, a halogen atom, a hydroxyl group, a mercapto group, an oxo group, a substituted oxy group (e.g., an alkoxy group, an aryloxy group, an acyloxy group), a substituted thio group, a carboxyl group, a substituted oxycarbonyl group, a substituted or unsubstituted carbamoyl group, a cyano group, a nitro group, a substituted or unsubstituted amino group, a sulfo group, an alkyl group (e.g., methyl, ethyl, t-butyl group or another $C_1$–$C_4$ alkyl group), an alkenyl group (e.g., a $C_2$–$C_4$ alkenyl group), analkynyl group (e.g., a $C_2$–$C_4$ alkynyl group), an alicyclic hydrocarbon group, an aromatic hydrocarbon group, and a heterocyclic group. Separately, an aromatic or non-aromatic ring (a hydrocarbon ring or a heterocyclic ring) may be condensed to the aforementioned rings.

Typical examples of the ketones represented by the formula (2) include acetone, methyl ethyl ketone, methyl isopropyl ketone, methyl isobutyl ketone, methyl s-butyl ketone, methyl t-butyl ketone, methyl decyl ketone, ethyl isopropyl ketone, isopropyl butyl ketone, methyl vinyl ketone, methyl isopropenyl ketone, methyl cyclohexyl ketone, methyl phenyl ketone, methyl 2-methylphenyl ketone, methyl 2-pyridyl ketone, cyclohexyl phenyl ketone, and other chain ketones; cyclopropanone, cyclobutanone, cyclopentanone, cyclohexanone, 4-methylcyclohexanone, 4-chlorocyclohexanone, isophorone, cycloheptanone, cyclooctanone, cyclodecanone, cyclododecanone, cyclopentadecanone, 1,3-cyclohexanedione, 1,4-cyclohexanedione, 1,4-cyclooctanedione, 2,2-bis(4-oxocyclohexyl)propane, bis(4-oxocyclohexyl)methane, 4-(4-oxocyclohexyl) cyclohexanone, 2-adamantanone, and other cyclic ketones.

The substrates used in the invention include not only compounds fed from outside into a reaction system but also compounds formed in the system under reaction conditions. By way of illustration, when a secondary alcohol is subjected to the reaction, a corresponding ketone formed by the reaction is included in the substrate, and the unreacted secondary alcohol coexistent in this step serves as a co-oxidizing agent.

According to the inventive production process 1 of esters or lactones, the use of a chain ketone as the substrate yields a corresponding ester, and the use of a cyclic ketone as the substrate yields a corresponding lactone having members one more than the material ketone. The inventive production process 1 of esters or lactones is especially useful as a process of oxidizing 3- to 20-membered cycloalkanones (cycloalkanones; e.g., cyclohexanones) which may have an alkyl group or another substituent, or cyclic ketones corresponding to bridged cyclic hydrocarbons each having about 2 to 4 rings to form corresponding lactones (e.g., ε-caprolactones).

Alcohols corresponding to the ketones represented by the formula (2) are represented by the formula (4). When such alcohols are used as the substrates, they are oxidized to corresponding ketones in the reaction system, and are further oxidized to target esters or lactones.

Separately, in the inventive production process 2 of esters or lactones, secondary alcohols represented by the formula (4) are used as the substrate. The secondary alcohols include secondary alcohols corresponding to the ketones mentioned as the substrate in the production process 1 of esters or lactones.

According to the production process 2 of esters or lactones, the use of a chain alcohol yields a corresponding ester, and the use of a cyclic alcohol gives a corresponding lactone having members one more than the material alcohol. The inventive production process 2 of esters or lactones is especially useful as a process of oxidizing 3- to 20-membered cycloalkanols (cycloalkanols; e.g., cyclohexanols) which may have an alkyl group or another substituent, or cyclic alcohols corresponding to bridged cyclic hydrocarbons each having about 2 to 4 rings to form corresponding lactones (e.g., ε-caprolactones) directly.

[Imide Compound]

Of the substituents $R^1$ and $R^2$ in the imide compound represented by the formula (1), the halogen atom includes iodine, bromine, chlorine and fluorine. The alkyl group includes, for instance, methyl, ethyl, propyl, isopropyl, butyl, isobutyl, s-butyl, t-butyl, pentyl, hexyl, heptyl, octyl, and decyl groups, and other straight- or branched-chain alkyl groups each having about 1 to 10 carbon atoms. As preferred alkyl groups, there may be mentioned, for instance, alkyl groups each having about 1 to 6 carbon atoms, and more preferably lower alkyl groups each having about 1 to 4 carbon atoms.

The aryl group includes phenyl, and naphthyl groups, for example; and the illustrative cycloalkyl group includes cyclopentyl, and cyclohexyl groups. As the alkoxy group, there may be mentioned, for example, methoxy, ethoxy, propoxy, isopropoxy, butoxy, isobutoxy, t-butoxy, pentyloxy and hexyloxy groups, and other alkoxy groups each having about 1 to 10 carbon atoms, preferably about 1 to 6 carbon atoms, of which lower alkoxy groups each having about 1 to 4 carbon atoms are especially preferred.

Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl and hexyloxycarbonyl groups, and other alkoxycarbonyl groups each having about 1 to 10 carbon atoms in the alkoxy moiety. Preferred alkoxycarbonyl groups include alkoxycarbonyl groups each having about 1 to 6 carbon atoms in the alkoxy moiety, and especially lower alkoxycarbonyl groups each having about 1 to 4 carbon atoms in the alkoxy moiety.

As the illustrative acyl group, there may be mentioned formyl, acetyl, propionyl, butyryl, isobutyryl, valeryl, isovaleryl, and pivaloyl groups, and other acyl groups each having about 1 to 6 carbon atoms.

The substituents $R^1$ and $R^2$ may be identical to or different from each other. The substituents $R^1$ and $R^2$ in the formula (1) may be combined to form a double bond, or an aromatic or non-aromatic ring. The preferred aromatic or non-aromatic ring is a 5- to 12-membered ring, and especially a 6- to 10-membered ring. It may be a heterocyclic ring or condensed heterocyclic ring, but it is often a hydrocarbon ring. Such rings include, for example, non-aromatic alicyclic rings (e.g., cyclohexane ring and other cycloalkane rings which may have a substituent, cyclohexene ring and other cycloalkene rings which may have a substituent), non-aromatic bridged rings (e.g., 5-norbornene ring and other bridged hydrocarbon rings which may have a substituent), benzene ring, naphthalene ring and other aromatic rings (including condensed rings) which may have a substituent. The ring is composed of an aromatic ring in many instances. The ring may have a substituent such as an alkyl group, a haloalkyl group, a hydroxyl group, an alkoxy group, a carboxyl group, an alkoxycarbonyl group, an acyl group, a nitro group, a cyano group, an amino group, or a halogen atom.

In the formula (1), X represents an oxygen atom or a hydroxyl group, and the bond between the nitrogen atom, N, and X is a single bond or a double bond.

On $R^1$, $R^2$, or on the double bond or aromatic or non-aromatic ring formed together by $R^1$ and $R^2$, one or two N-substituted cyclic imido groups indicated in the formula (1) may further be formed. By way of illustration, when $R^1$ or $R^2$ is an alkyl group having 2 or more carbon atoms, the N-substituted cyclic imido group may be formed together with adjacent two carbon atoms constituting the alkyl group. Likewise, when $R^1$ and $R^2$ are combined to form a double bond, the N-substituted cyclic imido group may be formed together with the double bond. In case that $R^1$ and $R^2$ are combined to form an aromatic or non-aromatic ring, the N-substituted cyclic imido group may be formed with adjacent two carbon atoms constituting the aforementioned ring.

Preferred imide compounds include compounds represented by the following formulae:

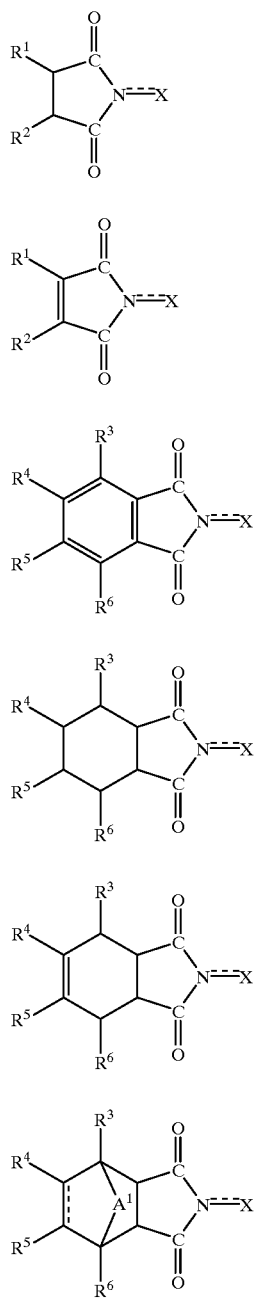

(wherein each of $R^3$ to $R^6$ is, identical to or different from each other, a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom; and, of $R^3$ to $R^6$ adjacent groups may be combined to form an aromatic or non-aromatic ring; in the formula (1f), $A^1$ represents a methylene group or an oxygen atom, and $R^1$ and $R^2$ have the same meanings as defined above; and one or two N-substituted cyclic imido groups Indicated in the formula (1c) may further be formed on the benzene ring in the formula (1c)).

In the substituents $R^3$ to $R^6$, the alkyl group includes similar alkyl groups to those exemplified above, especially alkyl groups having about 1 to 6 carbon atoms. The haloalkyl group includes trifluoromethyl group and other haloalkyl groups each having about 1 to 4 carbon atoms, and the alkoxy group includes similar alkoxy groups to those mentioned above, and especially lower alkoxy groups each having about 1 to 4 carbon atoms. The alkoxycarbonyl group includes similar alkoxycarbonyl groups to those described above, particularly lower alkoxycarbonyl groups each having about 1 to 4 carbon atoms in the alkoxy moiety. As the acyl group, there may be mentioned similar acyl groups to those described above, especially acyl groups each having about 1 to 6 carbon atoms, and the illustrative halogen atoms include fluorine, chlorine and bromine atoms. The substituents $R^3$ to $R^6$ are each a hydrogen atom, a lower alkyl group having about 1 to 4 carbon atoms, a carboxyl group, a nitro group, or a halogen atom in many instances. The ring formed together by $R^3$ to $R^6$ includes similar rings to the aforementioned rings which are formed together by $R^1$ and $R^2$. Among them, aromatic or non-aromatic 5- to 12-membered rings are particularly preferred.

As illustrative preferred imide compounds, there may be mentioned N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphthalenetetracarboximide.

The imide compounds represented by the formula (1) can be prepared by a conventional imidation reaction, for example by a process in which a corresponding acid anhydride is reacted with hydroxylamine, $NH_2OH$, and the acid anhydride group is ring-opened and then is ring-closed to give an imide.

Such acid anhydrides include succinic anhydride, maleic anhydride and other saturated or unsaturated aliphatic dicarboxylic anhydrides, tetrahydrophthalic anhydride, hexahydrophthalic anhydride (1,2-cyclohexanedicarboxylic anhydride), 1,2,3,4-cyclohexanetetracarboxylic 1,2-dianhydride, and other saturated or unsaturated non-aromatic cyclic polycarboxylic anhydrides (alicyclic polycarboxylic anhydrides), HET anhydride (chlorendic anhydride), himic anhydride, and other bridged cyclic polycarboxylic anhydride, (alicyclic polycarboxylic anhydrides), phthalic anhydride, tetrabromophthalic anhydride, tetrachlorophthalic anhydride nitrophthalic anhydride, trimellitic anhydride, methylcyclohexenetricarboxylic anhydride, pyromellitic anhydride, mellitic anhydride, 1,8;4,5-naphthalenetetracarboxylic dianhydride, and other aromatic polycarboxylic anhydrides.

Typically preferred imide compounds include N-hydroxyimide compounds derived from alicyclic polycarboxylic anhydrides or aromatic polycarboxylic anhydrides, of which N-hydroxyphthalimide and other N-hydroxyimide compounds derived from aromatic polycarboxylic anhydrides are especially preferred.

Each of the imide compounds represented by the formula (1) can be used singly or in combination. The imide compounds can be used as being supported by carriers. As such carriers, activated carbon, zeolite, silica, silica-alumina, bentonite and other porous carries are frequently employed.

The amount of the imide compound can be selected within a wide range, and is, for example, from about 0.0001 to 1 mole, preferably from about 0.001 to 0.5 mole, and more preferably from about 0.01 to 0.4 mole relative to 1 mole of the substrate. It is frequently used in an amount ranging from about 0.05 to 0.35 mole relative to 1 mole of the substrate.

[Promoter (Co-catalyst)]

In the inventive processes (in especial, the process for co-oxidation of organic compounds, the process for the production of epoxy compounds, and the production process 1 of esters or lactones), the promoter (co-catalyst) (C) can be used in combination with the catalyst represented by the formula (1) to improve or enhance the rate and selectivity of the reaction. Such promoters (C) include, but are not limited to, (C1) compounds each having a carbonyl group combined with an electron attractive group, (C2) metallic compounds, and (C3) organic salts each composed of a polyatomic cation or a polyatomic anion and its counter ion, which polyatomic cation or anion contains a Group 15 or Group 16 element of the Periodic Table of Elements having at least one organic group bonded thereto. Each of these promoters (C) can be used singly or in combination among the same kinds of promoters or the different kinds of promoters. For example, a combination of one or more compounds (C1) each having a carbonyl group combined with an electron attractive group, and one or more metallic compounds (C2) can be employed.

In the compounds (C1) each having a carbonyl group combined with an electron attractive group, the electron attractive group combined to the carbonyl group includes, but is not limited to, fluoromethyl, trifluoromethyl, tetrafluoroethyl, phenyl, fluorophenyl, pentafluorophenyl, and other hydrocarbon groups each substituted with a fluorine atom. As practical examples of the compounds (C1), there may be mentioned hexafluoroacetone, trifluoroacetic acid, pentafluorophenyl methyl ketone, pentafluorophenyl trifluoromethyl ketone, and benzoic acid. These compounds are typically useful when primary or secondary alcohols (a) are used as co-oxidizing agents. Furthermore, the use of these compounds in the oxidation of (A2) ketones or alcohols corresponding to the ketones promotes the rate of a Baeyer-Villiger type reaction. This is probably because these compounds are converted into highly reactive peroxides in the system.

The proportion of the compound (C1) falls in the range from about 0.0001 to 1 mole, preferably from about 0.001 to 0.7 mole, and more preferably from about 0.01 to 0.5 mole relative to 1 mole of the substrate.

Metallic elements to constitute the metallic compounds (C2) include, but are not limited to, any of metallic elements of the Groups 1 to 15 of the Periodic Table of Elements. In the present description, the term "metallic element" also means and includes boron, B. Examples of the metallic elements include, of the Periodic Table of Elements, Group 1 elements (e.g., Li, Na, K), Group 2 elements (e.g., Mg, Ca, Sr, Ba), Groups 3 elements (e.g., Sc, lanthanoid elements, actinoid elements), Group 4 elements (e.g., Ti, Zr, Hf), Group 5 elements (e.g., V), Group 6 elements (e.g., Cr, Mo, W), Group 7 elements (e.g., Mn), Group 8 elements (e.g., Fe, Ru), Group 9 elements (e.g., Co, Rh), Group 10 elements (e.g., Ni, Pd, Pt), Group 11 elements (e.g., Cu), Group 12 elements (e.g., Zn), Groups 13 elements (e.g., B, Al, In), Group 14 elements (e.g., Sn, Pb), Group 15 elements (e.g., Sb, Bi) and the like. Preferred metallic elements include transition metal elements (elements of Groups 3 to 12 of the Periodic Table of Elements). Among them, elements of the Groups 5 to 11 of the Periodic Table of Elements are preferred, of which elements of Group 6, Group 7 and Group 9 are typically preferred. Especially, Mo, Co and Mn are preferred. The valence of the metallic element is not particularly limited. The metallic elements have a valence of about 0 to 6 in many instances.

As the metallic compounds (C2), there may be mentioned, for example, elementary substances, hydroxides, oxides (including complex oxides), halides (fluorides, chlorides, bromides, iodides), salts of oxoacids (e.g., nirates, sulfates, phosphates, borates, carbonates), oxoacids, isopolyacids, heteropolyacids, and other inorganic compounds of the aforementioned metallic elements; salts of organic acids (e.g., acetates, propionates, prussiates, naphthenates, stearates), complexes, and other organic compounds of the metallic elements. Ligands constituting the complexes include OH (hydroxo), alkoxy (e.g., methoxy, ethoxy, propoxy, butoxy), acyl (e.g., acetyl, propionyl), alkoxycarbonyl (e.g., methoxycarbonyl, ethoxycarbonyl), acetylacetonato, cyclopentadienyl group, halogen atoms (e.g., chlorine, bromine), CO, CN, oxygen atom, $H_2O$ (aquo), phosphine (triphenylphosphine and other triarylphosphines) and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds.

Concrete examples of the metallic compounds (C2) include, by taking cobalt compounds as example, cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, and other salts of organic acids; cobalt acetylacetonato, and other complexes, and other divalent or trivalent cobalt compounds. As illustrative vanadium compounds, there may be mentioned vanadium hydroxide, vanadium oxide, vanadium chloride, vanadyl chloride, vanadium sulfate, vanadyl sulfate, sodium vanadate, and other inorganic compounds; vanadium acetylacetonato, vanadyl acetylacetonato, and other complexes, and other vanadium compounds having a valence of 2 to 5. Examples of molybdenum compounds include molybdenum hydroxide, molybdenum oxide, molybdenum chloride, molybdenum bromide, molybdenum sulfide, molybdic acid or its salts, phosphomolybdic acid or its salts, silicomolybdic acid or its salts, and other inorganic acids; molybdenum carbonyl, bis (acetylacetonato)dioxomolybdenum, chlorotricarbonyl($\eta$-cyclopentadienyl)molybdenum, dibromobis($\eta$-cyclopentadienyl)molybdenum, and other complexes, and other molybdenum compounds having a valence of 0 to 6. Examples of compounds of the other metallic elements include compounds corresponding to the above-mentioned cobalt, vanadium or molybdenum compounds.

Each of the metallic compounds (C2) can be used independently or in combination. In especial, when a compound (b) having a carbon-hydrogen bond at the adjacent position to an unsaturated bond is used as a co-oxidizing agent in the oxidation of the compound (A1) having a non-aromatic ethylenic bond, the combination use of molybdenum carbonyl or another molybdenum compound with cobalt acetate or another cobalt compound or manganese acetate or another manganese compound can give an epoxy compound in high yield. In the oxidation of (A2) the ketone or the alcohol corresponding to the ketone, the combination use of a compound containing V, Mo, Co, Mn, or another transition metal (other than Fe) with a compound containing a platinum group metallic element (Ru, Rh, Pd, Os, Ir, or Pt) or Fe as the metallic compounds (C2) can markedly improve the selectivity and give a target compound in high yield. In this case, a combination use of a Co compound with Pt(dppb) $(\mu\text{-OH})]_2(BH_4)_2$ or another platinum group metal hydrogen complex compound is typically preferred.

The proportion of the metallic compound (C2) is, for instance, about 0.0001 to 0.7 mole, preferably about 0.001 to 0.5 mole, and more preferably about 0.002 to 0.1 mole relative to 1 mole of the substrate. The metallic compound (C2) is frequently used in a proportion of about 0.005 to 0.05 mole relative to 1 mole of the substrate. If a molybdenum compound is used in combination with a cobalt compound or a manganese compound, the proportion of the molybdenum compound is within the range similar to the above range, but the proportion of the cobalt compound or manganese compound is, for example, about 0.0001 to 0.1 mole, and preferably about 0.0005 to 0.1 mole relative to 1 mole of the substrate.

In the organic salts (C3), the Group 15 elements of the Periodic Table of Elements include N, P, As, Sb, and Bi, and the Group 16 elements of the Periodic Table of Elements include, for example, O, S, Se and Te. Preferred elements are N, P, As, Sb, and S, of which N, P and S are typically preferred.

The organic groups to be bonded to atoms of the elements include, but are not limited to, hydrocarbon groups which may have a substituent, and substituted oxy groups. As the hydrocarbon groups, there may be mentioned, for instance, methyl, ethyl, propyl, isopropyl, butyl, isobutyl, s-butyl, t-butyl, pentyl, hexyl, octyl, decyl, tetradecyl, hexadecyl, octadecyl, allyl, and other straight- or branched-chain aliphatic hydrocarbon groups (alkyl groups, alkenyl groups and alkynyl groups) each having about 1 to 30 carbon atoms (preferably having about 1 to 20 carbon atoms); cyclopentyl, cyclohexyl, and other alicyclic hydrocarbon groups each having about 3 to 8 carbon atoms; and phenyl, naphthyl, and other aromatic hydrocarbon groups each having about 6 to 14 carbon atoms. Substituents which the hydrocarbon groups may have include, but are not limited to, a halogen atom, an oxo group, a hydroxyl group, a substituted oxy group (e.g., an alkoxy group, an aryloxy group, an acyloxy group), a carboxyl group, a substituted oxycarbonyl group, a substituted or unsubstituted carbamoyl group, a cyano group, a nitro group, a substituted or unsubstituted amino group, an alkyl group (e.g., methyl, ethyl, or another $C_1$–$C_4$ alkyl group), a cycloalkyl group, an aryl group (e.g., phenyl, ornaphthyl group), and aheterocyclic group. The preferred hydrocarbon groups include, for instance, alkyl groups each having about 1 to 30 carbon atoms, and aromatic hydrocarbon groups (especially, phenyl group or naphthyl group) each having about 6 to 14 carbon atoms. The substituted oxy groups include, but are not limited to, alkoxy groups, aryloxy groups and aralkyloxy groups.

The polyatomic cation is, for example, represented by the following formula (5). This polyatomic cation constitutes, with a counter anion, an organic onium salt represented by the following formula (6).

 (5)

 (6)

In the above formulae, RC is a hydrocarbon group or a hydrogen atom. The four $R^c$s may be identical to or different from each other, and at least one $R^c$ is a hydrocarbon group. The symbol A is an atom of Group 15 or Group 16 element of the Periodic Table of Elements. Two $R^c$s may be combined to form a ring with the adjacent A, or two $R^c$s may together form a double bond as one with A and simultaneously be combined with another $R^c$ to form a ring with A. The symbol m denotes 3 or 4. $Y^-$is a counter anion, and Y is an acid radical. The above hydrocarbon group may have any of the aforementioned substituents.

The rings which are formed by two $R^c$s with the adjacent A include, but are not limited to, pyrrolidine ring, piperidine ring, and other nitrogen--containing (or phosphorus-containing) heterocyclic rings each having about 3 to 8 members (preferably 5 or 6 members). Alternatively, two $R^c$s may together form a double bond as one with A and be combined with another $R^c$ to form a ring with A. Such rings just mentioned above include pyridine ring, and other 5- to 8-membered nitrogen-containing heterocyclic rings. To these rings, a benzene ring or another ring may be condensed. Such a condensed ring includes, for example, quinoline ring. In many cases, m is 4 when A is an atom of Group 15 elements of the Periodic Table of Elements, and, m is 3 when A is an atom of Group 16 elements of the Periodic Table of Elements.

The atom A is preferably N, P, As, Sb or S, more preferably N, P or S, and particularly N or P. In the preferred polyatomic cations, all the four $R^c$s are organic groups (including cases where a ring containing A is formed).

Examples of the acid radical Y include, but are not limited to, fluorine atom, chlorine atom, bromine atom, iodine atom, and other halogen atoms; nitrate radical ($NO_3$), sulfate radical ($So_4$), phosphate radical ($PO_4$), perchlorate radical ($ClO_4$), and other inorganic acid radicals; acetate radical ($CH_3CO_2$), methanesulfonate radical, benzenesulfonate radical, and other organic acid radicals. Preferred acid radicals include halogen atoms and inorganic acid radicals, of which chlorine atom, bromine atom and other halogen atoms are typically desirable.

Of the organic onium salts, typically preferred are organic ammonium salts, organic phosphonium salts, and organic sulfonium salts, for instance. As concrete examples of organic ammonium salts, there may be mentioned tetramethylammonium chloride, tetraethylammonium chloride, tetrabutylammonium chloride, tetrahexylammonium chloride, trioctylmethylammonium chloride, triethylphenylammonium chloride, tributyl(hexadecyl)ammonium chloride, di(octadecyl)dimethylammonium chloride, and other quaternary ammonium chlorides, and corresponding quaternary ammonium bromides, and other quaternary ammonium salts each having four hydrocarbon groups bonded to its nitrogen atom; dimethylpiperidinium chloride, hexadecylpyridinium chloride, methyl quinolinium chloride, and other cyclic quaternary ammonium salts.

Practical examples of the organic phosphonium salts include tetramethylphosphonium chloride, tetrabutylphosphonium chloride, tributyl(hexadecyl)phosphonium chloride, triethylphenylphosphonium chloride, and other quaternary phosphonium chlorides, and corresponding quaternary phosphonium bromides, and other quaternary phosphonium salts each having four hydrocarbon groups bonded to its phosphorus atom. Concrete examples of the organic sulfonium salts include triethylsulfonium iodide, ethyl-diphenylsulfonium iodide, and other sulfonium salts each having three hydrocarbon groups bonded to its sulfur atom.

The polyatomic anion is represented by, for example, the following formula (7). This polyatomic anion constitutes, with a counter cation, an organic salt represented by the following formula (8).

$$[R^dAO_3]^{q-} \quad (7)$$

$$Z^{q+}[R^dAO_3]^{q-} \quad (8)$$

In the above formulae, $R^d$ is a hydrocarbon group or a hydrogen atom; A is an atom of Group 15 or Group 16 element of the Periodic Table of Elements; q denotes 1 or 2; and $Z^{q+}$ is a counter cation.

Such hydrocarbon groups represented by $R^d$ include, in addition to similar groups to the above groups, resins (polymer chains or their branched chains). Preferred A includes, but is not limited to, S and P. The numeral q is 1 when A is S or the like, and it is 2 when A is P or the like. As Z, there may be mentioned, for instance, sodium, potassium, and other alkali metals; magnesium, calcium, and other alkaline earth metals, of which alkali metals are preferred. The counter cation $Z^{q+}$ may be the polyatomic cation as mentioned above.

Illustrative organic salts represented by the formula (8) include methanesulfonates, ethanesulfoneates, octanesulfonates, dodecanesulfonates, and other alkyl-sulfonates; benzenesulfonates, p-toluenesulfonates, naphthalenesulfonates, decylbenzenesulfonates, dodecylbenzenesulfonates, and other aryl-sulfonates which may be substituted with an alkyl group; sulfonic acid type ion exchange resins (ion exchangers); and phosphonic acid type ion exchange resins (ion exchangers). Of these salts, a $C_6$–$C_{18}$ alkyl-sulfonate, or a $C_6$–$C_{18}$ a alkyl-aryl sulfonate is used in many cases.

The amount of the organic salt (C3) falls in the range, for example, from about 0.0001 to 0.7 mole, preferably from about 0.001 to 0.5 mole, more preferably from about 0.002 to 0.1 mole and frequently from about 0.005 to 0.05 mole relative to 1 mole of the substrate. The use of the organic salt (C3) in an excess amount may reduce the reaction rate.

According to the invention, additional catalytic components or additives may be used. By way of illustration, Molecular Sieves such as Molecular Sieve 3A, Molecular Sieve 4A, or Molecular Sieve 5A may be added to the reaction system. The amount of the Molecular Sieve is, for example, about 1 to 1000 g, and preferably about 10 to 200 g relative to 1 mole of the substrate. The Molecular Sieve is frequently used in combination with the metallic compound (C2) or another promoter.

[Oxygen]

The molecular oxygen to be used for the oxidation of the substrate includes, but is not limited to, pure oxygen, and oxygen diluted with an inert gas such as nitrogen, helium, argon or carbon dioxide. Air is preferably used as the molecular oxygen from the points of operating property and safety, as well as cost efficiency.

The amount of the molecular oxygen can be chosen depending on the species of the substrate but is generally equal to or more than about 0.5 mole (e.g., equal to or more than 1 mole), preferably about 1 to 100 moles, and more preferably about 2 to 50 moles relative to 1 mole of the substrate. Excess moles of the molecular oxygen relative to the substrate is used in many cases.

[Co-oxidizing Agent (B)]

The compound (co-oxidizing agent) (B) which is oxidizable by the imide compound and oxygen has only to be a compound which is oxidizable by the imide compound and oxygen and is different from the compound to be used as the substrate. It may be either of same kinds as or of different kinds from that of the compound to be used as the substrate. The co-oxidizing agents (B) include compounds described as the substrates in Japanese Unexamined Patent Publication No. 8-38909 or Japanese Unexamined Patent Publication No. 9-327626 which discloses an oxidation reaction using the imide compound as a catalyst.

For example, as the co-oxidizing agent (B), use can be made of at least one compound selected from (a) primary or secondary alcohols, (b) compounds each having a carbon-hydrogen bond at the adjacent position to an unsaturated bond, (c) compounds each having a methine carbon atom, (d) cycloalkanes, (e) non-aromatic heterocyclic compounds each having a carbon-hydrogen bond at the adjacent position to a hetero atom, (f) conjugated compounds, (g) aromatic hydrocarbons, (h) thiols, (i) ethers, (j) sulfides, (k) aldehydes or thioaldehydes, and (1) amines. These compounds may have a variety of substituents. Such substituents include, but are not limited to, a halogen atom, an oxo group, a hydroxyl group, a mercapto group, a substituted oxy group (e.g., an alkoxy group, an aryloxy group, and an acyloxy group), a substituted thio group, a carboxyl group, a substituted oxy-carbonyl group, a substituted or unsubstituted carbamoyl group, a cyano group, a nitro group, a substituted or unsubstituted amino group, an alkyl group, an alkenyl group, an alkynyl group, a cycloalkyl group, a cycloalkenyl group, an aryl group (e.g., phenyl and naphthyl groups), an aralkyl group, and a heterocyclic group.

(a) Primary or Secondary Alcohols

The primary or secondary alcohols (a) include a wide variety of alcohols. These alcohols may be whichever of monohydric, dihydric or polyhydric.

Such primary alcohols include, but are not limited to, methanol, ethanol, 1-propanol, 1-butanol, 2-methyl-1-propanol, 1-pentanol, 1-hexanol, 1-octanol, 1-decanol, 1-hexadecanol, 2-buten-1-ol, ethylene glycol, trimethylene glycol, hexamethylene glycol, pentaerythritol, and other saturated or unsaturated aliphatic primary alcohols each having about 1 to 30 (preferably 1 to 20, and more preferably 1 to 15) carbon atoms; cyclopentylmethyl alcohol, cyclohexylmethyl alcohol, 2-cyclohexylethyl alcohol, and other saturated or unsaturated alicyclic primary alcohols; benzyl alcohol, 2-phenylethyl alcohol, 3-phenylpropyl alcohol, cinnamyl alcohol, and other aromatic primary alcohols; and 2-hydroxymethylpyridine, and other heterocyclic alcohols. Preferred primary alcohols include aliphatic primary alcohols (e.g., saturated aliphatic primary alcohols each having about 1 to 20 carbon atoms).

Illustrative secondary alcohols include 2-propanol, s-butyl alcohol, 2-pentanol, 3-pentanol, 2-hexanol, 2-octanol, 4-decanol, 2-hexadecanol, 2-penten-4-ol, and other saturated or unsaturated aliphatic secondary alcohols each having about 3 to 30 (preferably 3 to 20, and more preferably 3 to 15) carbon atoms; cyclobutanol, cyclopentanol, cyclohexanol, cyclooctanol, cyclododecanol, cyclopentadecanol, 2-cyclohexen-1-ol, 3,5,5-trimethyl-2-cyclohexen-1-ol, 1,3-cyclohexanediol, 1,4-cyclohexanediol, 1,4-cyclooctanediol, 2,2-bis(4-hydroxycyclohexyl)propane, bis(4-hydroxycyclohexyl)methane, 4-(4-hydroxycyclohexyl)cyclohexanol, and other saturated or unsaturated alicyclic secondary alcohols each having about 3 to 20 members (preferably 3 to 15 members, more preferably 5 to 15 members, and especially 5 to 8 members); 1-phenylethanol, 1-phenylpropanol, 1-phenylmethylethanol, diphenylmethanol (benzhydrol), and other aromatic secondary alcohols; and 1-(2-pyridyl)ethanol, and other heterocyclic secondary alcohols.

Preferred primary or secondary alcohols (a) include secondary alcohols (e.g., s-butyl alcohol and other aliphatic secondary alcohols, cyclohexanol and other alicyclic secondary alcohols, 1-phenylethanol (α-phenethyl alcohol), diphenylmethanol (benzhydrol) and other aromatic secondary alcohols). Each of these alcohols (a) can be used singly or in combination.

(b) Compounds Each Having a Carbon-hydrogen Bond at the Adjacent Position to an Unsaturated Bond As the compounds (b) each having a carbon-hydrogen bond at the adjacent position to an unsaturated bond, there may be mentioned, for example, (b1) aromatic compounds each having a methyl group or methylene group at the adjacent position to its aromatic ring (so-called benzyl position), and (b2) non-aromatic compounds each having a methyl group or methylene group at the adjacent position to an unsaturated bond (e.g., a carbon-carbon triple bond, a carbon-oxygen double bond).

In the aromatic compounds (b1), the aromatic ring may be either of an aromatic hydrocarbon ring or an aromatic heterocyclic ring. Such aromatic hydrocarbon rings include, but are not limited to, benzene ring, a condensed carbocyclic ring (e.g., naphthalene, azulene, indacene, anthracene, phenanthrene, triphenylene, pyrene, and other condensed carbocyclic rings in which two to ten 4- to 7-membered carbocyclic rings are condensed). As the aromatic heterocyclic rings, there may be mentioned, for instance, heterocyclic rings each containing an oxygen atom as a hetero atom (e.g., furan, oxazole, isoxazole and other 5-membered rings, 4-oxo-4H-pyran and other 6-membered rings, benzofuran, isobenzofuran, 4-oxo-4H-chromene and other condensed rings), heterocyclic rings each containing a sulfur atom as a hetero atom (e.g., thiophene, thiazole, isothiazole, thiadiazole, and other 5-membered rings, 4-oxo-4H-thiopyran, and other 6-membered rings, benzothiophene and other condensed rings), heterocyclic rings each containing a nitrogen atom as a hetero atom (e.g., pyrrole, pyrazole, imidazole, triazole, and other 5-membered rings, pyridine, pyridazine, pyrimidine, pyrazine, and other 6-membered rings, indole, quinoline, acridine, naphthyridine, quinazoline, purine, and other condensed rings).

The methylene group at the adjacent position to the aromatic ring may be a methylene group constituting a non-aromatic ring condensed to the aromatic ring. In the aromatic compounds (b1), both methyl group and methylene group can exist at the adjacent positions to the aromatic ring.

As examples of the aromatic compounds each having a methyl group at the adjacent position to an aromatic ring, there may be mentioned aromatic hydrocarbons having one to six methyl groups substituted to the aromatic ring (e.g., toluene, xylene, 1-ethyl-4-methylbenzene, 1-ethyl-3-methylbenzene, 1-t-butyl-4-methylbenzene, 1-methoxy-4-methylbenzene, mesitylene, durene, methylnaphthalene, methylanthracene, and 4,4'-dimethylbiphenyl), and heterocyclic compounds each having about one to six methyl groups substituted to its heterocyclic ring (e.g., 2-methylfuran, 3-methylfuran, 3-methythiophene, 2-methylpyridine, 3-methylpyridine, 4-methylpyridine, 2,4-dimethylpyridine, 2,4,6-trimethylpyridine, 4-methylindole, and 2-methylquinoline).

Illustrative aromatic compounds each having a methylene group at the adjacent position to its aromatic ring include, but are not limited to, aromatic hydrocarbons each having an alkyl group or substituted alkyl group having 2 or more carbon atoms (e.g., ethylbenzene, propylbenzene, 1,4-diethylbenzene, and diphenylmethane), aromatic heterocyclic compounds each having an alkyl group or substituted alkyl group having 2 or more carbon atoms (e.g., 2-ethylfuran, 3-propylthiophene, and 4-ethylpyridine, and 4-butylquinoline), and compounds in which a non-aromatic ring is condensed to an aromatic ring, and the non-aromatic ring has a methylene group at the adjacent position to the aromatic ring (e.g., dihydronaphthalene, indene, indan, tetralin, fluorene, acenaphthene, phenalene, indanone, and xanthene).

The non-aromatic compounds (b2) each having a methyl group or methylene group at the adjacent position to an unsaturated bond include, but are not limited to, (b2-1) unsaturated chain hydrocarbons each having a methyl group or a methylene group at the adjacent position to a carbon-carbon triple bond, and (b2-2) compounds each having a methyl group or methylene group at the adjacent position to a carbonyl group.

As the unsaturated chain hydrocarbons (b2-1), there may be mentioned, for example, methylacetylene, 2-butyne, and other alkynes each having about 3 to 20 carbon atoms. The compounds (b2-2) include, but are not limited to, ketones (e.g., acetone, methyl ethyl ketone, 3-pentanone, acetophenone, and other chain ketones; cyclohexanone and other cyclic ketones) and carboxylic acids or their derivatives (e.g., malonic acid, succinic acid, glutaric acid, and esters of these acids).

(c) Compounds Each Having a Methine Carbon Atom

The compounds (c) each having a methine carbon atom (or a tertiary carbon atom) include (c1) cyclic compounds each having a methine group (i.e., a methine carbon-hydrogen bond) as a constitutive unit of its ring, and (c2) chain compounds each having a methine carbon atom.

The cyclic compounds (c1) include, for example, (c1-1) bridged Cyclic compounds each having at least one methine group, and (c1-2) non-aromatic cyclic compounds (e.g., alicyclic hydrocarbons) each having a hydrocarbon group bonded to its ring. The bridged cyclic compounds also include compounds in which two rings commonly possess two carbon atoms, such as hydrogenated products of condensed polycyclic aromatic hydrocarbons.

The illustrative bridged cyclic compounds (c1-1) include decalin, bicyclo[2.2.0]hexane, bicyclo[2.2.2]octane, bicyclo[3.2.1]octane, bicyclo[4.3.2]undecane, thujone, carane, pinane, pinene, bornane, bornylene, norbornane, norbornene, camphor, camphoric acid, camphene, tricyclene, tricyclo[4.3.1.1$^{2,5}$]undecane, tricyclo[5.2.1.0$^{3,8}$]decane, exotricyclo[5.2.1.0$^{2,6}$] decane, endotricyclo[5.2.1.0$^{2,6}$]decane, endotricyclo[5.2.2.0$^{2,6}$]undecane, adamantane, 1-adamantanol, 1-chloroadamantane, 1-methyladamantane, 1,3-dimethyladamantane, 1-methoxyadamantane, 1-carboxyadamantane, 1-methoxycarbonyladamantane, 1-nitroadamantane, tetracyclo[4.4.0.1$^{2,5}$.1$^{7,10}$] dodecane, perhydroanthracene, perhydroacenaphthene, perhydrophenanthrene, perhydrophenalene, perhydroindene, quinuclidine, and other bridged cyclic hydrocarbons or bridged heterocyclic compounds each having 2 to 4 rings, and derivatives thereof. These bridged cyclic compounds each have a methine carbon atom at the bridgehead position (corresponding to a junction position when two rings commonly possess two atoms) Examples of the non-aromatic cyclic compounds (c1-2) each having a hydrocarbon group bonded to its ring include 1-methylcyclopentane, 1-methylcyclohexane, limonene, menthene, menthol, carbomenthone, menthone, and other 3- to 15-membered alicyclic hydrocarbons each having a hydrocarbon group (e.g., an alkyl group) bonded to its ring, and their derivatives. The hydrocarbon group just mentioned above contains about 1 to 20 (preferably 1 to 10) carbon atoms. The non-aromatic cyclic compounds (c1-2) each having a hydrocarbon group bonded to its ring each have a methine carbon atom at the bonding site between its ring and the hydrocarbon group.

Chain compounds (c2) each having a methine carbon atom includes chain hydrocarbons each having a tertiary carbon atom, such as isobutane, isopentane, isohexane, 3-methylpentane, 2,3-dimethylbutane, 2-methylhexane, 3-methylhexane, 3,4-dimethylhexane, 3-methyloctane, and other aliphatic hydrocarbons each having about 4 to 20 (preferably 4 to 10) carbon atoms, and their derivatives.

(d) Cycloalkanes

As the cycloalkanes (d), there may be mentioned compounds each having a 3- to 30-membered cycloalkane ring. Such compounds include, but are not limited to, cyclopropane, cyclobutane, cyclopentane, cyclohexane, cycloheptane, cyclooctane, cyclononane, cyclodecane, cyclododecane, cyclotetradecane, cyclohexadecane, cyclotetracosane, cyclotriacontane, and derivatives of these compounds. Preferred cycloalkane rings include 5- to 30-membered, particularly 5- to 20-membered cycloalkane rings.

(e) Non-aromatic Heterocyclic Compounds Each Having a Carbon-hydrogen Bond at the Adjacent Position to a Hetero Atom In the non-aromatic heterocyclic compounds (e) each having a carbon-hydrogen bond at the adjacent position to a hetero atom, non-aromatic heterocyclic rings include, but are not limited to, 3- to 20-membered (preferably 5- to 12-membered, and more preferably 5- or 6-membered) heterocyclic rings each having at least one hetero atom selected from a nitrogen atom, an oxygen atom and a sulfur atom. To each of the heterocyclic rings, one or two benzene rings, cyclohexane rings, pyridine rings or other aromatic or non-aromatic rings may be condensed. Examples of the heterocyclic rings include dihydrofuran, tetrahydrofuran, pyran, dihydropyran, tetrahydropyran, pyrrolidine, piperidine, piperazine, morpholine, indoline, chroman, and isochroman.

(f) Conjugated Compounds

The conjugated compounds (f) include, but are not limited to, (f1) conjugated dienes, (f2) α,β-unsaturated nitriles, and (f3) α,β-unsaturated carboxylic acids or derivatives (e.g., esters, amides and anhydrides) thereof.

As the conjugated dienes (f1), there may be mentioned, for instance, butadiene, isoprene, 2-chlorobutadiene, and 2-ethylbutadiene. The conjugated dienes (f1) also include, herein, vinyl acetylene and other compounds in which a double bond and a triple bond are conjugated. When the conjugated dienes (f1) are used as the co-oxidizing agents, the conjugated dienes (f1) are oxidized to, for example, alkenediols. For instance, the use of butadiene as the co-oxidizing agent yields 2-butene-1,4-diol, 1-butene-3,4-diol or the like.

The illustrative α,β-unsaturated nitriles (f2) are (meth)acrylonitrile and the like. The α,β-unsaturated carboxylic acids or derivatives thereof (f3) include, but are not limited to, (meth)acrylic acid; methyl (meth)acrylate, ethyl (meth)acrylate, isopropyl (meth)acrylate, butyl (meth)acrylate, 2-hydroxyethyl (meth)acrylate, and other (meth)acrylates; (meth)acrylamide, N-methylol(meth)acrylamide and other (meth)acrylamide derivatives.

(g) Aromatic Hydrocarbons

The aromatic hydrocarbons (g) include, but are not limited to, benzene, naphthalene, acenaphthylene, phenanthrene, anthracene, naphthacene, aceanthrylene, triphenylene, pyrene, chrysene, naphthacene, picene, perylene, pentacene, coronene, pyranthrene, ovalene, and other aromatic compounds each having at least one benzene ring. Of these compounds, preferred are condensed polycyclic aromatic compounds in which at least a plurality of benzene rings (e.g., two to ten benzene rings) are condensed.

These aromatic hydrocarbons may each have one or more substituents. Concrete examples of such aromatic compounds each having a substituent include 2-chloronaphthalene, 2-methoxynaphthalene, 1-methylnaphthalene, 2-methylnaphthalene, 2-methylanthracene, 2-t-butylanthracene, 2-carboxyanthracene, 2-ethoxycarbonylanthracene, 2-cyanoanthracene, 2-nitroanthracene, 2-methylpentalene. To each of the benzene rings, a non-aromatic carbon ring, an aromatic heterocyclic ring, or a non-aromatic heterocyclic ring may be condensed.

(h) Thiols

The thiols (h) include, but are not limited to, methanethiol, ethanethiol, 1-propanethiol, 1-butanethiol, 1-hexanethiol, 1-octanethiol, 1-decanethiol, 1-propenethiol, ethylene thioglycol, propylene thioglycol, 1,3-butanedithiol, and other aliphatic thiols; cyclopentanethiol, cyclohexanethiol, methylcyclohexanethiol, cyclohexene-1-thiol, and other alicyclic thiols; and phenylmethanethiol, 2-phenylethanethiol, and other aromatic thiols.

(i) Ethers

Examples of the ethers (i) include diethyl ether, dipropyl ether, diisopropyl ether, dibutyl ether, methyl ethyl ether, methyl butyl ether, ethyl butyl ether, diallyl ether, methyl vinyl ether, ethyl allyl ether, and other aliphatic ethers; and anisole, phenetole, dibenzyl ether, phenyl benzyl ether, and other aromatic ethers.

(j) Sulfides

The illustrative sulfides (j) include, but are not limited to, diethyl sulfide, dipropyl sulfide, diisopropyl sulfide, dibutyl sulfide, methyl ethyl sulfide, methyl butyl sulfide, ethyl butyl sulfide, diallyl sulfide, and other aliphatic sulfides; and methyl phenyl sulfide, ethyl phenyl sulfide, diphenyl sulfide, dibenzyl sulfide, phenyl benzyl sulfide, and other aromatic sulfides.

(k) Aldehydes or Thioaldehydes

Examples of the aldehydes are acetaldehyde, propionaldehyde, hexanal, decanal, succinaldehyde, glutaraldehyde, adipaldehyde, and other aliphatic aldehydes; formylcyclohexane, citral, citronellal, and other alicyclic aldehydes; benzaldehyde, nitrobenzaldehyde, cinnamaldehyde, salicylaldehyde, anisaldehyde, phthalaldehyde, isophthalaldehyde, terephthalaldehyde, and other aromatic aldehydes; furfural, nicotinic aldehyde, and other heterocyclic aldehydes. The thioaldehydes include thioaldehydes corresponding to the aforementioned aldehydes.

(l) Amines

The illustrative amines (l) are primary or secondary amines such as methylamine, ethylamine, propylamine, butylamine, dimethylamine, diethylamine, dibutylamine, ethylenediamine, 1,4-butanediamine, hydroxylamine, ethanolamine, and other aliphatic amines; cyclopentylamine, cyclohexylamine, and other alicyclic amines; benzylamine, toluidine, and other aromatic amines.

Of these co-oxidizing agents (B), preferred compounds are the (a) primary or secondary alcohols, (b) compounds each having a carbon-hydrogen bond at the adjacent position to an unsaturated bond, (c) compounds each having a methine carbon atom, and (d) cycloalkanes. In particular, typically preferred are secondary alcohols, and (b1) aromatic compounds each having a methyl group or methylene group at the adjacent position to its aromatic ring (a so-called benzyl position). Such preferred compounds (b1) include, but are not limited to, toluene, ethylbenzene, and other aromatic hydrocarbons each having a methyl group or methylene group at the adjacent position to an aromatic ring; and fluorene, tetralin, and other compounds each having a non-aromatic ring condensed to an aromatic ring, and having a methylene group at the adjacent position of the non-aromatic ring adjacent to the aromatic ring.

According to the invention, when the ketone represented by the formula (2) is used as the substrate, a secondary alcohol corresponding to the ketone, i.e., the compound represented by the formula (4) is preferably used as the co-oxidizing agent (B). In this case, the co-oxidizing agent is converted into the substrate in the system, and a target compound can be obtained with efficiency, and can be purified with facility.

Each of the co-oxidizing agents (B) can be used independently or in combination as a mixture. The proportion of the co-oxidizing agent (B) is, for example, about 0.1 to 200 moles, preferably about 0.5 to 100 moles, and more preferably about 1 to 50 moles (especially 2 to 30 moles) relative to 1 mole of the substrate. The co-oxidizing agent can be used as a reaction solvent. In this connection, when the substrate, e.g., the compound (A1) having a non-aromatic ethylenic bond, is available at low costs, it is economically advantageous to use the substrate in an excess amount relative to the co-oxidizing agent (B).

In the inventive processes, it is supposed that the co-oxidizing agent (e.g., a primary or secondary alcohol) is oxidized in the system to form a peroxide, and this peroxide is involved in the reaction of the compound having a non-aromatic ethylenic bond into an epoxy compound or of the ketone into an ester or a lactone.

In the production process 2 of esters or lactones, the oxidation reaction may be performed in the presence of a ketone. Such ketones include a wide variety of ketones (aliphatic ketones, alicyclic ketones and aromatic ketones) such as the ketones represented by the formula (2). The existence of a ketone in the system can give a target compound in high yield by an acid treatment in a successive step, probably because a stable peroxide is liable to generate. According to a preferred embodiment of the production process 2 of esters or lactones, a ketone corresponding to the substrate, the secondary alcohol represented by the formula (4), is used as the ketone. When such a ketone is used, a peroxide represented by the following formula (9):

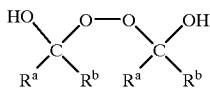

(9)

(wherein $R^a$ and $R^b$ have the same meanings as defined above) is formed as an intermediate in the oxidation reaction. The intermediate has a symmetric structure and can therefore give a single ester or lactone by the acid treatment. Accordingly, a target compound can be produced with efficiency and be purified with facility.

Each of the ketones may be employed singly or in combination. The proportion of the ketone is about 0 to 10 moles (e.g., 0.1 to 10 moles), preferably about 0.5 to 5 moles, and more preferably about 1 to 3 moles relative to 1 mole of the substrate.

[Oxidation Reaction]

The oxidation reaction is generally performed in an organic solvent. Such organic solvents include, but are not limited to, acetic acid, propionic acid, and other organic acids; acetonitrile, propionitrile, benzonitrile, and other nitrites; formamide, acetamide, dimethylformamide (DMF), dimethylacetamide, and other amides; hexane, octane, and other aliphatic hydrocarbons; chloroform, dichloromethane, dichloroethane, carbon tetrachloride, chlorobenzene, trifluoromethylbenzene (trifluorotoluene), and other halogenated hydrocarbons; nitrobenzene, nitromethane, nitroethane, and other nitro compounds; ethyl acetate, butyl acetate, and other esters; and mixtures of these solvents. In may cases, acetic acid and other organic acids, acetonitrile, benzonitrile, and other nitrites, trifluorobenzene, and other halogenated hydrocarbons, ethyl acetate and other esters are used as the solvent.

According to the inventive processes, the oxidation reaction smoothly proceeds even under comparatively mild conditions. The reaction temperature can adequately be selected depending on, for example, the species of the substrate, and is, for instance, about 0° C. to 300° C., preferably about 20° C. to 200° C., and more preferably about 30° C. to 150° C. The reaction is generally performed at a temperature ranging from about 40° C. to 100° C. The reaction can be carried out at atmospheric pressure or under pressure. When the reaction is conducted under pressure, the pressure is usually about 1 to 100 atm (e.g. 1.5 to 80 atm), preferably about 2 to 70 atm. The reaction time can adequately be selected within the range of, for example, 30 minutes to 48 hours according to the reaction temperature and pressure. The reaction can be performed in a batch system, semi-batch system, continuous system or another conventional system, in the presence of, or under flow of, molecular oxygen.

After the completion of the reaction, reaction products can be isolated and purified with facility in a conventional manner. Such a conventional manner includes, for example, filtration, concentration, distillation, extraction, crystallization, recrystallization, column chromatography and other isolation means, or any combination of these isolation means.

According to the invention, when the compound (A1) having a non-aromatic ethylenic bond is used as the substrate, the ethylenic bond (double bond) position of the compound is preferentially oxidized to give a corresponding epoxy compound in satisfactory yield. In especial, even if the substrate is an unsaturated compound (an allyl alcohol) having a hydroxyl group at its allyl position or its derivative (e.g., an unsaturated compound having an acyloxy group at its allyl position), a corresponding epoxy alcohol in which its ethylenic bond position is epoxidized in high yield. Separately, when (A2) the ketone represented by the formula (2) or an alcohol corresponding to the ketone is used as the substrate, a Baeyer-Villiger type reaction proceeds to give a corresponding ester or lactone in satisfactory yield.

The co-oxidizing agent (B) is usually oxidized under reaction conditions to give a corresponding oxidized product. For instance, the primary or secondary alcohols are generally converted into aldehydes, carboxylic acids or ketones by the reaction. In the aromatic compounds (b1) each having a methyl group or methylene group at the adjacent position to its aromatic ring, the methyl group or methylene group is oxidized to give corresponding alcohols, aldehydes, ketones or carboxylic acids (predominantly, alcohols).

By utilizing this mechanism and using the aromatic compound (b1) having a methyl group or methylene group at the adjacent position to its aromatic ring as the co-oxidizing agent (B), the compound (A1) having a non-aromatic ethylenic bond can yield a corresponding epoxy compound with markedly high efficiency. To be more specific, the oxidation of the compound (A1) having a non-aromatic ethylenic bond, in the coexistence of the aromatic compound (b1) having a methyl group or methylene group at the adjacent position to its aromatic ring/ gives a corresponding epoxy compound with an alcohol (a primary or secondary alcohol) corresponding to the aromatic compound (b1) [a first-stage reaction]. As mentioned above, the alcohol formed in this stage also serves as the co-oxidizing agent (B), one more molecule of the epoxy compound is formed from the substrate, the compound (A1) having a non-aromatic ethylenic bond [a second-stage reaction]. To be more specific, when propene (propylene) is oxidized in the coexistence of ethylbenzene (co-oxidizing agent), propylene oxide and α-phenethyl alcohol are formed in the first-stage reaction, and the α-phenethyl alcohol serves as another co-oxidizing agent in the second-stage reaction to give one more molecule of propylene oxide from propene. In this stage, the α-phenethyl alcohol is converted into acetophenone. According to this process, two molecules of an epoxy compound can be formed from one molecule of the aromatic compound (b1) through one-pot. In this case, the proportion of the compound (A1) having a non-aromatic ethylenic bond is preferably equal to or more than 2 moles relative to 1 mole of the aromatic compound (b1) having a methyl group or methylene group at the adjacent position to its aromatic ring.

[Acid treatment]

In the inventive production process 2 of esters or lactones, reaction products are treated with an acid after the oxidation reaction. The acid includes protonic acids and Lewis acids. As examples of such protonic acids there may be mentioned sulfuric acid, hydrochloric acid, phosphoric acid, methanesulfonic acid, and p-toluenesulfonic acid. Examples of the Lewis acids include cerium chloride, titanium chloride, zirconium chloride, vanadyl chloride, iron chloride, cobalt chloride, rhodium chloride, nickel chloride, copper chloride, copper acetate, zinc chloride, cadmium chloride, aluminum chloride, aluminum bromide, indium chloride, tin chloride, and other salts (including halides) of Groups 3 to 15 metals of the Periodic Table of Elements. Preferred acids include Lewis acids, especially, indium chloride, and other halides of Groups 3 to 15 metals of the Periodic Table of Elements (particularly Group 13 metals of the Periodic Table of Elements). Each of these acids can be used independently or in combination as a mixture.

The amount of the acid is, for example, about 0.001 to 1 mole, preferably about 0.01 to 0.7 mole, and more preferably about 0.05 to 0.5 mole relative to 1 mole of the substrate. The treatment temperature is, for example, about −10° C. to 50° C., and preferably about 0° C. to 30° C. The reaction is generally performed at or around room temperature in many cases.

The acid treatment is usually performed in an organic solvent. As the organic solvent, the solvents to be used in the oxidation reaction can be employed. In the production process 2 of esters or lactones, the reaction mixture obtained by the oxidation reaction may be subjected to the acid treatment as intact or may be subjected to the acid treatment after an adequate treatment such as solvent-exchange.

In general, when the secondary alcohol represented by the formula (4) is oxidized by molecular oxygen in the presence of the imide compound represented by the formula (1), a peroxide, an intermediate of the oxidation reaction, (e.g., the compound represented by the formula (9)) may frequently be remained. According to the inventive production process 2 of esters or lactones, probably because the peroxide is rapidly decomposed into a target corresponding ester or lactone, the target compound can be obtained in satisfactory yield. In this connection, only a heating treatment (e.g., at about 30° C. to 100° C.) of the oxidized product without the use of an acid can decompose the peroxide to improve the yield of the ester or lactone.

After the completion of the reaction, the reaction product can be isolated and purified with facility by a conventional method such as the aforementioned isolation means. The production process 2 of esters or lactones is very useful as a process for obtaining esters or lactones directly from secondary alcohols.

According to the inventive process for the co-oxidation of organic compounds, alkenes, cycloalkenes, and other compounds each having a non-aromatic ethylenic bond, and chain or cyclic ketones can be oxidized, under mild conditions, by simple operations with efficiency.

The inventive process for the production of epoxy compounds can provide corresponding epoxy compounds from compounds each having a non-aromatic ethylenic bond, under mild conditions, by simple operations in satisfactory yield.

According to the inventive processes for the production of esters or lactones, corresponding esters or lactones can be obtained, under mild conditions, from ketones (or their corresponding alcohols) or secondary alcohols by simple operations with efficiency.

The present invention will now be described in more detail with reference to several examples below which are not directed to limiting the scope of the invention.

EXAMPLE 1

A mixture of 2 mmol of 2,4,4-trimethyl-2-pentene, 20 mmol of 1-phenylethanol (α-phenethyl alcohol), 0.4 mmol of N-hydroxyphthalimide, 0.1 mmol of hexafluoroacetone trihydrate, and 2 ml of benzonitrile was stirred at 70° C. under an oxygen atmosphere (1 atm) for 16 hours. Gas chromatographic analysis of products in a reaction mixture revealed that 2,4,4-trimethyl-2-pentene was converted, at a rate of 55%, into 2,4,4-trimethyl-2,3-epoxypentane in yield of 43%.

EXAMPLE 2

A mixture of 2 mmol of 2-octene (a mixture of cis-isomer and trans-isomer), 20 mmol of 1-phenylethanol (α-phenethyl alcohol), 0.6 mmol of N-hydroxyphthalimide, 0.6 mmol of hexafluoroacetone trihydrate, and 2 ml of trifluoromethylbenzene was stirred at 90° C. under an oxygen atmosphere (1 atm) for 22 hours. Gas chromatographic analysis of products in a reaction mixture revealed that 2-octene was converted, at a rate of 91%, into 2,3-epoxyoctane in yield of 70%.

EXAMPLE 3

A mixture of 2 mmol of 2-octene (a mixture of cis-isomer and trans-isomer), 10 mmol of 1-phenylethanol (α-phenethyl alcohol), 0.2 mmol of N-hydroxyphthalimide, 0.4 mmol of hexafluoroacetone trihydrate, 0.001 mmol of cobalt (II) acetate, and 2 ml of trifluoromethylbenzene was stirred at 70° C. under an oxygen atmosphere (1 atm) for 16 hours. Gas chromatographic analysis of products in a reaction mixture revealed that 2-octene was converted, at a rate of 77%, into 2,3-epoxyoctane in yield of 56%.

EXAMPLE 4

A mixture of 4 mmol of 2-octene (a mixture of cis-isomer and trans-isomer), 20 mmol of tetralin, 0.4 mmol of N-hydroxyphthalimide, 0.2 mmol of molybdenum hexacarbonyl, 0.004 mmol of cobalt (II) acetate, 200 mg of Molecular Sieve 4A, and 2 ml of benzonitrile was stirred at 50° C. under an oxygen atmosphere (1 atm) for 20 hours.

Gas chromatographic analysis of products in a reaction mixture revealed that 2-octene was converted, at a rate of 82%, into 2,3-epoxyoctane in yield of 72%, and that tetralin was converted, at a rate of 42%, into α-tetralol (yield: 21%) and α-tetralone (yield: 43%).

EXAMPLE 5

A mixture of 4 mmol of cis-2-octene, 20 mmol of tetralin, 0.4 mmol of N-hydroxyphthalimide, 0.2 mmol of molybdenum hexacarbonyl, 0.004 mmol of cobalt (II) acetate, 200 mg of Molecular Sieve 4A, and 2 ml of benzonitrile was stirred at 50° C. under an oxygen atmosphere (1 atm) for 14 hours. Gas chromatographic analysis of products in a reaction mixture revealed that 2-octene was converted, at a rate of 83%, into 2,3-epoxyoctane (cis/trans=98.5/1.5) in yield of 72%, and that tetralin was converted, at a rate of 35%, into α-tetralol (yield: 34%) and α-tetralone (yield: 46%).

EXAMPLE 6

A mixture of 2 mmol of 2-octene (a mixture of cis-isomer and trans-isomer), 10 mmol of tetralin, 0.2 mmol of N-hydroxyphthalimide, 0.04 mmol of molybdenum hexacarbonyl, and 2 ml of benzonitrile was stirred at 80° C. under an oxygen atmosphere (1 atm) for 20 hours. Gas chromatographic analysis of products in a reaction mixture revealed that 2-octene was converted, at a rate of 67%, into 2,3-epoxyoctane in yield of 42%.

EXAMPLE 7

A mixture of 2 mmol of 2-octene (a mixture of cis-isomer and trans-isomer), 10 mmol of tetralin, 0.2 mmol of N-hydroxyphthalimide, 0.1 mmol of molybdenum hexacarbonyl, 0.002 mmol of manganese (II) acetate, and 2 ml of benzonitrile was stirred at 70° C. under an oxygen atmosphere (1 atm) for 5 hours. Gas chromatographic analysis of products in a reaction mixture revealed that 2-octene was converted, at a rate of 67%, into 2,3-epoxyoctane in yield of 53%. In this connection, tetralin was found to be converted, at a rate of 20%, into α-tetralol (yield: 8.2%) and α-tetralone (yield: 8.3%).

EXAMPLE 8

A mixture of 2 mmol of 2-octene (a mixture of cis- and trans-isomers), 10 mmol of tetralin, 0.2 mmol of N-hydroxyphthalimide, 0.1 mmol of molybdenum hexacarbonyl, 0.002 mmol of cobalt (II) acetate, and 2 ml of acetonitrile was stirred at 70° C. under an oxygen atmosphere (1 atm) for 5 hours. Gas chromatographic analysis of products in a reaction mixture revealed that 2-octene was converted, at a rate of 56%, into 2,3-epoxyoctane in yield of 49%. In this connection, tetralin was found to be converted, at a rate of 23%, into α-tetralol (yield: 7.7%) and α-tetralone (yield: 10%).

EXAMPLE 9

The procedure of Example 8 was repeated, except that 2 ml of ethyl acetate was used instead of acetonitrile, to give 2,3-epoxyoctane in yield of 40% at a conversion rate from 2-octene of 51%.

EXAMPLE 10

A mixture of 4 mmol of 2-octene (a mixture of cis- and trans-isomers), 40 mmol of ethylbenzene, 0.4 mmol of N-hydroxyphthalimide, 0.2mmol of molybdenum hexacarbonyl, 0.004 mmol of cobalt (II) acetate, 200 mg of Molecular Sieve 4A, and 2 ml of benzonitrile was stirred at 60° C. under an oxygen atmosphere (1 atm) for 12 hours. Gas chromatographic analysis of products in a reaction mixture revealed that 2-octene was converted, at a rate of 81%, into 2,3-epoxyoctane in yield of 57%.

EXAMPLE 11

A mixture of 4 mmol of 2-octene (a mixture of cis- and trans-isomers), 60 mmol of toluene, 0.4 mmol of N-hydroxyphthalimide, 0.2mmol of molybdenum hexacarbonyl, 0.004 mmol of cobalt (II) acetate, 200 mg of Molecular Sieve 4A, and 2 ml of benzonitrile was stirred at 70° C. under an oxygen atmosphere (1 atm) for 6 hours. Gas chromatographic analysis of products in a reaction mixture revealed that 2-octene was converted, at a rate of 59%, into 2,3-epoxyoctane in yield of 26%.

EXAMPLE 12

A mixture of 4 mmol of cyclohexene, 40 mmol of ethylbenzene, 0.4 mmol of N-hydroxyphthalimide, 0.2 mmol of molybdenum hexacarbonyl, 0.004 mmol of cobalt (II) acetate, 200 mg of Molecular Sieve 4A, and 2 ml of benzonitrile was stirred at 60° C. under an oxygen atmosphere (1 atm) for 12 hours. Gas chromatographic analysis of products in a reaction mixture revealed that cyclohexene was converted, at a rate of 84%, into cyclohexene oxide (yield: 72%), cyclohexanone (yield: 4%), and cyclohexanol (yield: 2%).

EXAMPLE 13

To 3 ml of trifluoromethylbenzene were added 3 mmol of 1-octene, 15 mmol of benzhydrol, 0.3 mmol of N-hydroxyphthalimide, and 0.6 mmol of hexafluoroacetone trihydrate, and the resultant mixture was stirred at 90° C. under an oxygen atmosphere (1 atm) for 24 hours. Gas chromatographic analysis of products in a reaction mixture revealed that 1-octene was converted, at a rate of 80%, into 1,2-epoxyoctane in yield of 72%.

EXAMPLE 14

A mixture of 3 mmol of 2-octene (a mixture of cis-isomer and trans-isomer), 15 mmol of benzhydrol, 0.3 mmol of N-hydroxyphthalimide, 0.0015 mmol of cobalt (II) acetate, 0.3 mmol of hexafluoroacetone trihydrate, and 3 ml of trifluoromethylbenzene was stirred at 60° C. under an oxygen atmosphere (1 atm) for 18 hours. Gas chromatographic analysis of products in a reaction mixture revealed that 2-octene was converted, at a rate of 82%, into 2,3-epoxyoctane in yield of 77%.

EXAMPLE 15

A mixture of 3mmol of cis-2-octene, 15mmol of benzhydrol, 0.3 mmol of N-hydroxyphthalimide, 0.0015 mmol of cobalt (II) acetate, 0.3 mmol of hexafluoroacetone trihydrate, and 3 ml of trifluoromethylbenzene was stirred at 60° C. under an oxygen atmosphere (1 atm) for 22 hours. Gas chromatographic analysis of products in a reaction mixture revealed that cis-2-octene was converted, at a rate of 91%, into cis-2,3-epoxyoctane in yield of 84%.

EXAMPLE 16

A mixture of 3 mmol of cyclooctene, 15 mmol of benzhydrol, 0.3 mmol of N-hydroxyphthalimide, 0.0015 mmol of cobalt (II) acetate, 0.3 mmol of hexafluoroacetone trihydrate, and 3 ml of trifluoromethylbenzene was stirred at 60° C. under an oxygen atmosphere (1 atm) for 22 hours. Gas chromatographic analysis of products in a reaction mixture revealed that cyclooctene was converted, at a rate of 88%, into cyclooctene oxide in yield of 83%.

EXAMPLE 17

A mixture of 3 mmol of cis-3-hexen-1-ol, 15 mmol of benzhydrol, 0.3 mmol of N-hydroxyphthalimide, 0.0015 mmol of cobalt (II) acetate, 0.3 mmol of hexafluoroacetone trihydrate, and 3 ml of trifluoromethylbenzene was stirred at 60° C. under an oxygen atmosphere (1 atm) for 18 hours. Gas chromatographic analysis of products in a reaction mixture revealed that cis-3-hexen-1-ol was converted, at a rate of 90%, into cis-3,4-epoxy-1-hexanol (yield: 74%).

EXAMPLE 18

A mixture of 3 mmol of trans-2-hexen-1-ol, 15 mmol of benzhydrol, 0.3 mmol of N-hydroxyphthalimide, 0.0015 mmol of cobalt (II) acetate, 0. 6 mmol of hexafluoroacetone trihydrate, and 3 ml of trifluoromethylbenzene was stirred at 50° C. under an oxygen atmosphere (1 atm) for 24 hours. Gas chromatographic analysis of products in a reaction mixture revealed that trans-2-hexen-1-ol was converted, at a rate of 82%, into trans-2,3-epoxy-1-hexanol (yield: 73%).

EXAMPLE 19

A mixture of 3mmol of 1-octen-3-ol, 15mmol of benzhydrol, 0.3 mmol of N-hydroxyphthalimide, 0.0015 mmol of cobalt (II) acetate, 0.6 mmol of hexafluoroacetone trihydrate, and 3 ml of trifluoromethylbenzene was stirred at 60° C. under an oxygen atmosphere (1 atm) for 24 hours. Gas chromatographic analysis of products in a reaction mixture revealed that 1-octen-3-ol was converted, at a rate of 43%, into 1,2-epoxy-3-octanol (yield: 40%).

EXAMPLE 20

A mixture of 3mmol of 1-p-menthene, 15mmol of benzhydrol, 0.3 mmol of N-hydroxyphthalimide, 0.0015 mmol of cobalt (II) acetate, 0.3 mmol of hexafluoroacetone trihydrate, and 3 ml of trifluoromethylbenzene was stirred at 60° C. under an oxygen atmosphere (1 atm) for 12 hours. Gas chromatographic analysis of products in a reaction mixture revealed that 1-p-menthene was converted, at a rate of 63%, into 1-p-menthene oxide (yield: 42%).

EXAMPLE 21

A mixture of 2 mmol of trans-1-acetoxy-3,7-dimethyl-2, 6-octadiene, 10 mmol of benzhydrol, 0.2 mmol of N-hydroxyphthalimide, 0.2 mmol of hexafluoroacetone trihydrate, and 4 ml of benzonitrile was stirred at 80° C. under an oxygen atmosphere (1 atm) for 20 hours. Gas chromatographic analysis of products in a reaction mixture revealed that trans-1-acetoxy-3,7-dimethyl-2,6-octadiene was converted, at a rate of 88%, into trans-1-acetoxy-6,7-epoxy-3,7-dimethyl-2-octene (yield: 71%).

EXAMPLE 22

A mixture of 2 mmol of cis-1-acetoxy-3,7-dimethyl-2,6-octadiene, 10 mmol of benzhydrol, 0.2 mmol of N-hydroxyphthalimide, 0.2 mmol of hexafluoroacetone trihydrate, and 4 ml of benzonitrile was stirred at 80° C. under an oxygen atmosphere (1 atm) for 20 hours. Gas chromatographic analysis of products in a reaction mixture revealed that cis-1-acetoxy-3,7-dimethyl-2,6-octadiene was converted, at a rate of 90%, into cis-1-acetoxy-6,7-epoxy-3,7-dimethyl-2-octene (yield: 75%).

EXAMPLE 23

To a mixture of 1 mole of ethylbenzene, 0.1 mole of N-hydroxyphthalimide, 1 mmol of cobalt (II) acetate and 1 l of benzonitrile was added 3 moles of propylene, and the resultant mixture was stirred at 80° C. under oxygen atmosphere (oxygen:

1 atm) for 6 hours. Gas chromatographic analysis of products in a reaction mixture revealed that 1.95 mole of propylene oxide was formed, and that acetophenone (yield 92%: on ethylbenzene basis) and α-phenethyl alcohol (yield 7%: on ethylbenzene basis) were produced. The conversion rate from ethylbenzene was 99%.

EXAMPLE 24

To a mixture of 1 mole of α-phenethyl alcohol, 0.1 mole of N-hydroxyphthalimide, 1 mmol of cobalt (II) acetate and 1 l of benzonitrile was added 1.5 moles of propylene, and the resultant mixture was stirred at 80° C. under oxygen atmosphere (oxygen: 1 atm) for 6 hours. Gas chromatographic analysis of products in a reaction mixture revealed that 0.92 mole of propylene oxide was formed, and that acetophenone (yield 98%: on α-phenethyl alcohol basis) was produced. The conversion rate from (x-phenethyl alcohol was 99%.

EXAMPLE 25

A mixture of 2 mmol of cyclohexanone, 20 mmol of cyclohexanol, 0.4 mmol of N-hydroxyphthalimide, 0.6 mmol of hexafluoroacetone trihydrate and 1 ml of benzonitrile was stirred at 80° C. under oxygen atmosphere (1 atm) for 12 hours. Gas chromatographic analysis of products in a reaction mixture revealed that 1.532 mmol (yield 76.6% on cyclohexanone basis) of α-caprolactone was produced. The reaction mixture contained 5.83 mmol of cyclohexanone and 11.87 mmol (conversion rate: 40%) of cyclohexanol.

EXAMPLE 26

A mixture of 2 mmol of cyclohexanone, 20 mmol of cyclohexanol, 0.4 mmol of N-hydroxyphthalimide, 0.6 mmol of hexafluoroacetonetrihydrate, 0.001 mmol of cobalt (II) acetate, and 1 ml of benzonitrile was stirred at 70° C. under oxygen atmosphere (1 atm) for 12 hours. Gas chromatographic analysis of products in a reaction mixture revealed that 0.612 mmol (yield 32.2% on cyclohexanone basis) of ε-caprolactone was produced. The reaction mixture contained 5.15 mmol of cyclohexanone and 16.54 mmol (conversion rate: 17%) of cyclohexanol.

EXAMPLE 27

A mixture of 2 mmol of cyclohexanone, 20 mmol of cyclohexanol, 0.2 mmol of N-hydroxyphthalimide, 0.6 mmol of hexafluoroacetone trihydrate and 3 ml of benzonitrile was stirred at 80° C. under oxygen atmosphere (1 atm) for 12 hours. Gas chromatographic analysis of products in a reaction mixture revealed that ε-caprolactone was produced in yield of 54.0% (on cyclohexanone basis). The reaction mixture contained 5.08 mmol of cyclohexanone and 13.83 mmol (conversion rate: 31%) of cyclohexanol.

EXAMPLE 28

A mixture of 3 mmol of cyclohexanone, 3 mmol of cyclohexanol, 0.3 mmol of N-hydroxyphthalimide, 1.5 mmol of hexafluoroacetone trihydrate and 5 ml of benzonitrile was stirred at 80° C. under oxygen atmosphere (1 atm) for 20 hours. Gas chromatographic analysis of products in a reaction mixture revealed that ε-caprolactone was produced in yield of 38.4% (on cyclohexanone basis). The reaction mixture contained 3.00 mmol of cyclohexanone and 1.05 mmol (conversion rate: 65%) of cyclohexanol.

EXAMPLE 29

The procedure of Example 25 was repeated, except that 4-methylcyclohexanone (2 mmol) and 4-methylcyclohexanol (20 mmol) were respectively used instead of cyclohexanone and cyclohexanol. As a result, γ-methyl-ε-caprolactone was formed in yield of 45.6% (on 4-methylcyclohexanone basis).

EXAMPLE 30

The procedure of Example 29 was repeated, except that cyclohexanol (20 mmol) was used instead of 4-methylcyclohexanol to give γ-methyl-ε-caprolactone in yield of 54.8% (on 4-methylcyclohexanone basis). In the reaction mixture were formed cyclohexanone (yield: 41.7% on cyclohexanol basis) and ε-caprolactone (yield: 4.4% on cyclohexanol basis).

EXAMPLE 31

By repeating the procedure of Example 25 except that cyclopentadecanone (2 mmol) was used instead of cyclohexanone, 15-pentadecanolide was formed in yield of 42.6% (on cyclopentadecanone basis). In the reaction mixture were formed cyclohexanone (yield: 52.4% on cyclohexanol basis) and ε-caprolactone (yield: 4.2% on cyclohexanol basis).

EXAMPLE 32

A mixture of 2 mmol of 2-methylcyclohexanone, 10 mmol of benzhydrol, 0.4 mmol of N-hydroxyphthalimide, 0.4 mmol of hexafluoroacetone trihydrate, and 2 ml of trifluoromethylbenzene (trifluorotoluene) was stirred at 70° C. under an oxygen atmosphere (1 atm) for 18 hours. Gas chromatographic analysis of products in a reaction mixture revealed that 2-methylcyclohexanone was converted, at a rate of 86%, into ε-methyl-ε-caprolactone in yield of 50% (on 2-methylcyclohexanone basis).

EXAMPLE 33

A mixture of 1 mmol of 2-methylcyclohexanone, 5 mmol of benzhydrol, 0.05 mmol of N-hydroxyphthalimide, 0.005 mmol of cobalt (II) acetate, 0.02 mmol of [Pt(dppb)($\mu$-OH)]$_2$(BH$_4$)$_2$, and 2 ml of ethyl acetate was stirred at 40° C. under an oxygen atmosphere (1 atm) for 23 hours. Gas chromatographic analysis of products in a reaction mixture revealed that 2-methylcyclohexanone was converted, at a conversion rate of 49%, into ε-methyl-ε-caprolactone in yield of 46% (on 2-methylcyclohexanone basis) at a selectivity of 94%.

EXAMPLE 34

A mixture of 1 mmol of 2-methylcyclohexanone, 5 mmol of benzhydrol, 0.1 mmol of N-hydroxyphthalimide, 0.002 mmol of cobalt (II) acetate, 0.02 mmol of [Pt(dppb)($\mu$-OH)]$_2$(BH$_4$)$_2$ and 2 ml of ethyl acetate was stirred at 40° C. under an oxygen atmosphere (1 atm) for 23 hours. Gas chromatographic analysis of products in a reaction mixture revealed that 2-methylcyclohexanone was converted, at a conversion rate of 64%, into ε-methyl-ε-caprolactone in yield of 60% (on 2-methylcyclohexanone basis) at a selectivity of 93%.

EXAMPLE 35

A mixture of 1 mmol of 2-methylcyclohexanone, 5 mmol of benzhydrol, 0.05 mmol of N-hydroxyphthalimide, 0.002 mmol of cobalt (II) acetate, 0.02 mmol of [Pt(dppb)($\mu$-OH)]$_2$(BH$_4$)$_2$ and 1 ml of ethyl acetate was stirred at 40° C. under an oxygen atmosphere (1 atm) for 23 hours. Gas chromatographic analysis of products in a reaction mixture revealed that 2-methylcyclohexanone was converted, at a conversion rate of 64%, into ε-methyl-ε-caprolactone in yield of 60% (on 2-methylcyclohexanone basis) at a selectivity of 93%.

EXAMPLE 36

A mixture of 1 mmol of cyclohexanone, 5 mmol of benzhydrol, 0.1 mmol of N-hydroxyphthalimide, 0.001 mmol of cobalt (II) acetate, 0.02 mmol of [Pt(dppb)($\mu$-OH)]$_2$(BH$_4$)$_2$ and 2 ml of trifluoromethylbenzene was stirred at 50° C. under an oxygen atmosphere (1 atm) for 18 hours. Gas chromatographic analysis of products in a reaction mixture revealed that cyclohexanone was converted, at a conversion rate of 24%, into ε-caprolactone in yield of 21% (on cyclohexanone basis) at a selectivity of 88%.

EXAMPLE 37

A mixture of 1 mmol of cyclohexanone, 5 mmol of benzhydrol, 0.1 mmol of N-hydroxyphthalimide, 0.001 mmol of cobalt (II) acetate, 0.02 mmol of [Pt(dppb)($\mu$-OH)]$_2$(BH$_4$), and 2 ml of dichloroethane (DCE) was stirred at 50° C. under an oxygen atmosphere (1 atm) for 23 hours. Gas chromatographic analysis of products in a reaction mixture revealed that cyclohexanone was converted, at a conversion rate of 46%, into ε-caprolactone in yield of 26% (on cyclohexanone basis) at a selectivity of 57%.

EXAMPLE 38

A mixture of 3 mmol of cyclohexanol, 0.3 mmol of N-hydroxyphthalimide, and 2 ml of acetonitrile was stirred at 75° C. under an oxygen atmosphere (1 atm) for 18 hours. To the obtained reaction mixture was added 0.6 mmol of indium chloride (InCl$_3$), and the resultant mixture was stirred at room temperature for 5 hours. Gas chromatographic analysis of products in a reaction mixture revealed that ε-caprolactone was formed in an amount of 0.264 mmol (yield on cyclohexanol basis: 8.8%). The reaction mixture also contained 1.60 mmol (conversion rate: 47%) of cyclohexanol and 0.526 mmol of cyclohexanone.

EXAMPLE 39

A mixture of 3 mmol of cyclohexanol, 3 mmol of cyclohexanone, 0.3 mmol of N-hydroxyphthalimide, and 2 ml of acetonitrile was stirred at 750C. under an oxygen atmosphere (1 atm) for 18 hours. To the obtained reaction mixture was added 0.6 mmol of indium chloride (InCl$_3$), and the resultant mixture was stirred at room temperature for 5 hours. Gas chromatographic analysis of products in a reaction mixture revealed that ε-caprolactone was formed in an amount of 0.711 mmol (yield on cyclohexanol basis: 24%). The reaction mixture also contained 0.349 mmol (conversion rate: 88%) of cyclohexanol and 3.73 mmol of cyclohexanone.

EXAMPLE 40

A mixture of 3 mmol of cyclohexanol, 6 mmol of cyclohexanone, 0.3 mmol of N-hydroxyphthalimide, and 1 ml of acetonitrile was stirred at 75° C. under an oxygen atmosphere (1 atm) for 14 hours. To the obtained reaction mixture was added 0.6 mmol of indium chloride (InCl₃), and the resultant mixture was stirred at room temperature for 5 hours. Gas chromatographic analysis of products in a reaction mixture revealed that ε-caprolactone was formed in yield on cyclohexanol basis of 31%. The conversion rate from cyclohexanol was 95%.

EXAMPLE 41

A mixture of 3 mmol of cyclohexanol, 6 mmol of cyclohexanone, 0.3 mmol of N-hydroxyphthalimide, and 1 ml of acetonitrile was stirred at 75° C. under an oxygen atmosphere (1 atm) for 14 hours. To the obtained reaction mixture was added 1.0 mmol of indium chloride (InCl₃), and the resultant mixture was stirred at room temperature for 5 hours. Gas chromatographic analysis of products in a reaction mixture revealed that there were formed ε-caprolactone in yield of 32%, a peroxide (a precursor of ε-caprolactone) represented by the following formula:

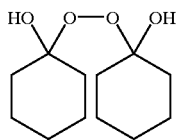

in yield of 14% (60% in terms of ε-caprolactone), and cyclohexanone in yield of 26%. The yields were all figures on cyclohexanol basis. The conversion rate from cyclohexanol was 88%.

What is claimed is:

1. A process for the production of epoxy compounds, esters, or lactones, said process comprising the step of:

oxidizing (A) a compound selected from (A1) a compound having a non-aromatic ethylenic bond and (A2) a ketone represented by the following formula (2):

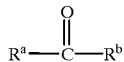

(2)

wherein each of $R^a$ and $R^b$ is, identical to or different from each other, an organic group having a carbon atom at a bonding site with the adjacent carbonyl carbon atom, where $R^a$ and $R^b$ may be combined to form a ring with the adjacent carbonyl carbon atom, or an alcohol corresponding to said ketone, by molecular oxygen in the presence of an imide compound represented by the following formula (1):

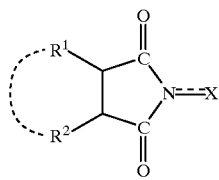

(1)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond, or an aromatic or non-aromatic ring; X is an oxygen atom or a hydroxyl group; and one or two N-substituted cyclic imido groups indicated in the formula (1) may further be formed on the aforementioned $R^1$, $R^2$, or on the double bond or aromatic or non-aromatic ring formed together by $R^1$ and $R^2$, and in the presence of (B) a compound being oxidizable by said imide compound and oxygen wherein said compound (B) is different from said compound (A).

2. A process for the co-oxidation of organic compounds according to claim 1, wherein $R^1$ and $R^2$ in said imide compound represented by the formula (1) are combined to form an aromatic or non-aromatic 5- to 12-membered ring.

3. A process for the co-oxidation of organic compounds according to claim 1, wherein $R^1$ and $R^2$ in said imide compound represented by the formula (1) are combined to form a cycloalkane ring which may have a substituent, a cycloalkene ring which may have a substituent, a bridged carbocyclic ring which may have a substituent, or an aromatic ring which may have a substituent.

4. A process for the co-oxidation of organic compounds according to claim 1, wherein said compound (A1) having a non-aromatic ethylenic bond is a compound selected from (A11) chain hydrocarbons each having an ethylenic bond and having 2 to 30 carbon atoms, (A12) compounds each having a 3- to 30-membered cycloalkene ring, (A13) unsaturated bridged cyclic hydrocarbons, and (A14) heterocyclic compounds each having a non-aromatic ethylenic bond as a constitutive element of its ring.

5. A process for the co-oxidation of organic compounds according to claim 1, wherein said ketone represented by the formula (2) is a 3- to 20-membered cycloalkanone.

6. A process for the co-oxidation of organic compound according to claim 1, wherein said ketone represented by the formula (2) is a cyclohexanone.

7. A process for the co-oxidation of organic compounds according to claim 1, wherein at least one compound selected from (a) primary or secondary alcohols, (b) compounds each having a carbon-hydrogen bond at the adjacent position to an unsaturated bond, (c) compounds each having a methine carbon atom, (d) cycloalkanes, (e) non-aromatic heterocyclic compounds each having a carbon-hydrogen bond at the adjacent position to a hetero atom, (f) conjugated compounds, (g) aromatic hydrocarbons, (h) thiols, (i) ethers, (j) sulfides, (k) aldehydes or thioaldehydes, and (l) amines, is used as said compound (B).

8. A process for the co-oxidation of organic compounds according to claim 1, wherein the oxidation is performed further in the presence of (C) at least one compound selected from the group consisting of (C1) compounds each having a carbonyl group combined with an electron attractive group, (C2) metallic compounds, and (C3) organic salts each composed of a polyatomic cation or a polyatomic anion and its counter ion, said polyatomic cation or polyatomic anion containing a Group 15 or Group 16 element of the Periodic Table of Elements, said element having at least one organic group bonded thereto.

9. A process for the production of epoxy compounds, said process comprising the step of:

oxidizing (A1) a compound having a non-aromatic ethylenic bond by molecular oxygen in the presence of an imide compound represented by the following formula (1):

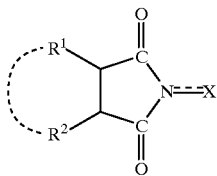

(1)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond, or an aromatic or non-aromatic ring; X is an oxygen atom or a hydroxyl groups and one or two N-substituted cyclic imido groups indicated in the formula (1) may further be formed on the aforementioned $R^1$, $R^2$, or on the double bond or aromatic or non-aromatic ring formed together by $R^1$ and $R^2$, to form a corresponding epoxide, wherein said compound (A1) having a non-aromatic ethylenic bond is oxidized in the presence of (B1) a compound being oxidizable by said imide compound and oxygen, said compound (B1) being different from said compound (A1)

thereby producing a compound having an epoxy group in place of said ethylenic bond.

10. A process for the production of esters or lactones, said process comprising the step of:

oxidizing (A2) a ketone represented by the following formula (2):

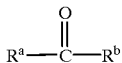

(2)

wherein each of $R^a$ and $R^b$ is, identical to or different from each other, an organic group having a carbon atom at a bonding site with the adjacent carbonyl carbon atom, where $R^a$ and $R^b$ may be combined to form a ring with the adjacent carbonyl carbon atom, or an alcohol corresponding to said ketone, by molecular oxygen in the presence of an imide compound represented by the following formula (1):

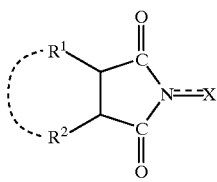

(1)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an aryl group, where $R^1$ and $R^2$ may be combined to form a double bond, or an aromatic or non-aromatic ring; X is an oxygen atom or a hydroxyl groups and one or two N-substituted cyclic imido groups indicated in the formula (1) may further be formed on the aforementioned $R^1$, $R^2$, or on the double bond or aromatic or non-aromatic ring formed together by $R^1$ and $R^2$, together with (B2) a compound being oxidizable by said imide compound and oxygen and being different from said compound (A2)

thereby producing a compound represented by the following formula (3):

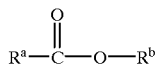

(3)

wherein each of $R^a$ and $R^b$ is, identical to or different from each other, an organic group having a carbon atom at a bonding site with the adjacent carbonyl carbon atom or oxygen atom, where $R^a$ and $R^b$ maybe combined to form a ring with the adjacent carbonyl carbon atom and oxygen atom.

11. A process for the production of esters or lactones according to claim 10, wherein a ketone represented by the formula (2) is used as a substrate, and a secondary alcohol corresponding to said ketone is used as said compound (B2).

12. A process for the production of esters or lactones, said process comprising the steps of:

oxidizing a secondary alcohol represented by the following formula (4):

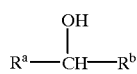

(4)

wherein each of $R^a$ and $R^b$ is, identical to or different from each other, an organic group having a carbon atom at a bonding site with the adjacent carbon atom, where $R^a$ and $R^b$ may be combined to form a ring with the adjacent carbon atom, by molecular oxygen in the presence of an imide compound represented by the following formula (1):

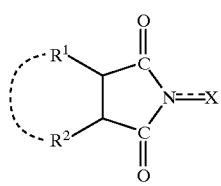

(1)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond, or an aromatic or non-aromatic ring; X is an oxygen atom or a hydroxyl group; and one or two N-substituted cyclic imido groups indicated in the formula (1) may further be formed on the aforementioned $R^1$, $R^2$, or on the double bond or aromatic or non-aromatic ring formed together by $R^1$ and $R^2$, and treating the oxidized compound with an acid thereby producing a compound represented by the following formula (3):

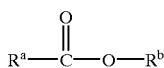
(3)

wherein each of $R^a$ and $R^b$ is, identical to or different from each other, an organic group having a carbon atom at a bonding site with the adjacent carbonyl carbon atom or oxygen atom, where $R^a$ and $R^b$ maybe combined to form a ring with the adjacent carbonyl carbon atom and oxygen atom.

13. A process for the production of esters or lactones according to claim 12, wherein the oxidation is performed in the presence of a ketone.

14. A process for the production of esters or lactones according to claim 13, wherein a ketone corresponding to the secondary alcohol represented by the formula (4) is used as said ketone.

15. A process for the production of esters or lactones according to claim 12, wherein a Lewis acid is used as said acid.

16. A process for the production of esters or lactones according to claim 12, wherein a 3- to 20-membered cycloalkanol is oxidized by molecular oxygen in the presence of said imide compound represented by the formula (1), and the oxidized compound is treated with an acid to give a corresponding lactone.

17. A process for the production of esters or lactones according to claim 12, wherein a cyclohexanol is oxidized by molecular oxygen in the presence of the imide compound represented by the formula (1), and the oxidized compound is treated with an acid to give a corresponding ε-caprolactone.

* * * * *